United States Patent [19]

Xu et al.

[11] Patent Number: 5,496,331
[45] Date of Patent: Mar. 5, 1996

[54] KNOT-FORMING INSTRUMENT AND METHOD OF FORMING KNOTS

[75] Inventors: Zhongren Xu; Masahiro Nudeshima, both of Kanagawa, Japan

[73] Assignee: Terumo Kabushiki Kaisha, Tokyo, Japan

[21] Appl. No.: 281,174

[22] Filed: Jul. 27, 1994

[30] Foreign Application Priority Data

Jul. 28, 1993 [JP] Japan ............................. 5-207310
Aug. 5, 1993 [JP] Japan ............................. 5-215099

[51] Int. Cl.⁶ ................................................ A61B 17/04
[52] U.S. Cl. ........................................... 606/139; 606/148
[58] Field of Search ........................................ 606/139, 148; 604/281; 289/17

[56] References Cited

U.S. PATENT DOCUMENTS

| 4,351,333 | 9/1982 | Lazarus et al. | 604/164 |
|---|---|---|---|
| 4,747,840 | 5/1988 | Ladika et al. | 604/281 |
| 4,874,360 | 10/1989 | Goldberg et al. | 604/8 |
| 4,913,683 | 4/1990 | Gregory | 604/8 |
| 5,050,715 | 8/1991 | Green et al. | 227/176 |
| 5,234,445 | 8/1993 | Walker et al. | 606/148 |
| 5,281,236 | 1/1994 | Bagnato et al. | 606/139 |
| 5,318,221 | 6/1994 | Green et al. | 227/178 |
| 5,330,491 | 7/1994 | Walker et al. | 606/148 |

FOREIGN PATENT DOCUMENTS

| 3-12126 | 1/1991 | Japan | A61B 17/10 |
|---|---|---|---|
| 6-189968 | 7/1994 | Japan | A61B 17/06 |

*Primary Examiner*—Gary Jackson
*Attorney, Agent, or Firm*—Burns, Doane, Swecker & Mathis

[57] ABSTRACT

A knot forming instrument forms a knot of a thread inside an abdominal cavity of a patient. This instrument includes an control rod to be inserted into a communicating tube which communicates the abdominal cavity and the outside of a body of the patient, an insertion path formed inside the control rod and having an opening formed at a tip portion of the control rod; thread introducing mechanism for introducing the thread into the insertion path from the opening; and a control device formed on the base portion for operating the control rod from the outside of the body. The tip portion of the control rod constitutes a bendable portion which can be deformed between a straight condition and a bent condition bent into a loop shape by the operation of the control device. In a preferred method, one end of the thread is held by the control rod and the tip portion thereof is bent so as to form the loop. Thereafter, the other end of the thread is inserted into the loop with another control rod to twist the ends of the thread, and a tension is applied to the thread to form a knot.

23 Claims, 28 Drawing Sheets

KNOT-FORMING INSTRUMENT AND METHOD OF FORMING KNOTS

BACKGROUND OF THE INVENTION

1. Field of the Invention

The present invention relates to the art of forming a knot of threads when carrying out suturing inside living bodies, and in particular relates to knot-forming instrument and method for forming a knot of threads used when tissue is sutured or when anastomosis or ligation is carried out inside an abdominal cavity during, for example, laparoscopic surgeries.

2. Background

In recent years, surgical operations such as appendectomies, gall bladder removals and the like have been performed by laparascopic methods that allow such operations to be carried out without the need to cut open the abdomen. To carry out such laparoscopic surgeries, a plurality of tubes known as trocar tubes are inserted into the abdominal cavity. Various instruments are inserted through these trocar tubes, including a camera that allows a surgeon to carry out the operation while viewing a monitor.

However, when suturing or ligation is carried out with current surgical instruments, it is a very time-consuming process. Stated more concretely, in order to form the suture or ligation, the thread must be pulled out with forceps or the like through one of the trocar tubes to the outside of the body in order to form a knot, which then must be passed back through the trocar tube to place the knot where it needs to be inside the abdominal cavity.

As a result, the operation becomes excessively laborious and time-consuming, and there is also the increased chance of infection.

In recent years, special instruments have been developed in the hopes of eliminating such problems. One example is the staple-type needle proposed by Laid-Open Patent Publication No. 3-12126 for carrying out anastomosis or suturing. However, there is the disadvantage that the staple is likely to be left inside the body. Further, there is also a danger that the stapler can be dropped inside the abdominal cavity due to faulty operation. Moreover, the stapler is not as strong as certain types of thread that could be used for suturing.

Furthermore, during standard surgical operations that require especially strong knots, such as when a thick blood vessel is to be ligated, it becomes necessary to wrap the thread 2 or 3 times. However, the staple means mentioned above cannot be employed for forming such knots. Moreover, to carry out such procedures with existing methods as descsribed above will result in the operation becoming even more laborious and time-consuming.

SUMMARY OF THE INVENTION

The first object of the present invention is, therefore, to provide a knot forming instrument and a knot forming method which can easily and securely form knots of a thread for use in suturing, anastomosis or ligation in a body cavity such as an abdominal cavity by means of remote control from the outside of the body.

The second object of the present invention is to provide a knot forming instrument and a knot forming method which can form a strong knot which is surely secured or placed to a body tissue.

In order to achieve these objects the present invention is directed to a knot forming instrument which comprises:

a control rod to be inserted into a communicating tube which communicates an abdominal cavity and the outside of a body of a patient, the control rod having a base portion and a tip portion;

an insertion path formed inside the control rod and having an opening formed at the tip portion of the control rod;

thread introducing means for introducing the thread into the insertion path from the opening; and a control device formed on the base portion for operating the control rod from the outside of the body, wherein the tip portion of the control rod constitutes a bendable portion which can be changed into a straight condition and a bent condition bent into at least one direction by the operation of the control device.

Preferably, the bendable portion can be bent so as to form one loop or two or more loops. By doing so, the knot of the thread can be formed with easy operation. In particular, when the bendable portion is constituted so as to form two or more loops, it becomes possible to carry out suturing, anastomosis or ligation with more steady knots. As a result, the number of operation for forming knots can be reduced to shorten the time required for such a surgical treatment, thus leading to reduced burden of a patient.

Preferably, the operation device is formed from at least one wire of which tip is secured to a position which is eccentrical to an axis of the bendable portion, and a bending motion control mechanism for operating the bendable portion by pulling wires toward base end thereof. In this case, the wires are wound around the bendable portion helically from the position where the tip ends of the wires are secured toward the bending motion control mechanism. By doing so, the loop of the bendable portion can be formed securely.

Further, if a suction means is used as the thread introducing means, it becomes possible to introduce the thread into the insertion path rapidly without injuring the body tissue, which results in reducing the number of the steps required for the surgical operation and therefore shortening the time required for the operation.

Furthermore, if a tensioning means for tensioning the thread is further provided, it becomes possible to produce a steady knot easily without performing any step for pulling the thread with a hand and to secure or place thus formed knot onto the body tissue stably and securely.

Moreover, if a thread cutting means is further provided, it becomes not necessary to additionally provide any instrument for cutting the thread and to locate the portions to be cut with such an instrument, which result in shortening the time required after the knot having been formed.

Alternatively, the knot forming apparatus according to the present invention may include:

a pair of control rods to be inserted into a communicating tube which communicates an abdominal cavity and the outside of a body of a patient;

Control devices formed on the respective base portions of the control rods for operating the operation rods from the outside of the body; and a binding member for binding the base portions of the control rods, wherein the tip portion of at least one control rod is formed into a bendable portion which is bendable by the operation of the control device between a straight condition and a bent condition in which the tip portion is bent into at least one direction.

According to this alternative, the handling of the instrument becomes easier and the number of the communication tubes required for the knot forming process can be reduced, thus leading to reduced burden of the patient.

Preferably, in this case, the control rod includes a bendable portion provided on the tip portion thereof for bending the tip portion into a predetermined shape under original condition thereof, and a regulating member for regulating the shape of the bendable portion into the straight. By doing so, any wires used for bending the bendable portion and any reels for pulling wires will be unnecessary. Therefore, the structure of the instrument can be simplified and the diameter of the control rod can be further reduced. Further, the operation required for bending the bendable portion can be also simplified. Furthermore, since the bendable portion is always bent into its predetermined original shape, the operation can be repeated with ease.

In addition, in order to achieve the above object, the present invention is also directed to the knot forming method which comprises the steps of:

inserting first and second control rods into the abdominal cavity through communicating tubes which communicate the abdominal cavity to the outside of a body, each of the control rods formed with an insertion path which extends therethrough;

introducing the first thread into the insertion path of the first control rod from the opening of the first control rod and holding the first thread;

bending a tip portion of the first control rod so as to form at least one loop by remote control from the outside of the body;

inserting the tip portion of the second operation rod into the loop;

introducing the second thread into the insertion path of the second control rod from the opening of the second control rod and holding the second thread;

inserting the second thread into the loop by pulling out the tip portion of the second control rod from the loop by retracting the second control rod;

crossing the first thread and the second thread to twist them with each other; and tensioning at least one of the first and second threads, wherein a first knot is formed by executing these steps.

According to this method, it becomes possible to form a knot of a thread with easy operation.

Preferably, the knot forming method further includes the steps of:

releasing the tensile condition of the first and second threads;

discharging one of the first and second threads outside the insertion path from the opening of the operation rod;

bending the tip portion of either of the first and second control rods so as to at least one loop by means of remote control from the outside of the body;

inserting the tip portion of the other control rod into the loop;

reintroducing the discharged thread into the insertion path of the control rod again and holding the thread;

pulling out the tip portion of the other operation rod from the loop by retracting the control rod and inserting the thread held by the control rod into the loop; and crossing the first thread and the second thread to twist them with each other; wherein a second knot is formed by executing these steps after the first knot has been formed.

In this ease, the second knot is preferably formed so as to have a different knot forming direction from that of the first knot. By doing so, there is less possibility that the knot will be loosened. As a result, it becomes possible to carry out suturing or ligation with a steady knot and the steps necessary for forming such knots can be performed easily.

The above and other objects, advantages and features of this invention will be more fully understood from the following detailed description, taken in conjunction with the drawings.

DETAILED DESCRIPTION OF THE PREFERRED EMBODIMENTS

With reference to the attached drawings, a detailed description of preferred embodiments of a knot forming instrument according to the present invention will now be described hereinbelow.

Figure 1:
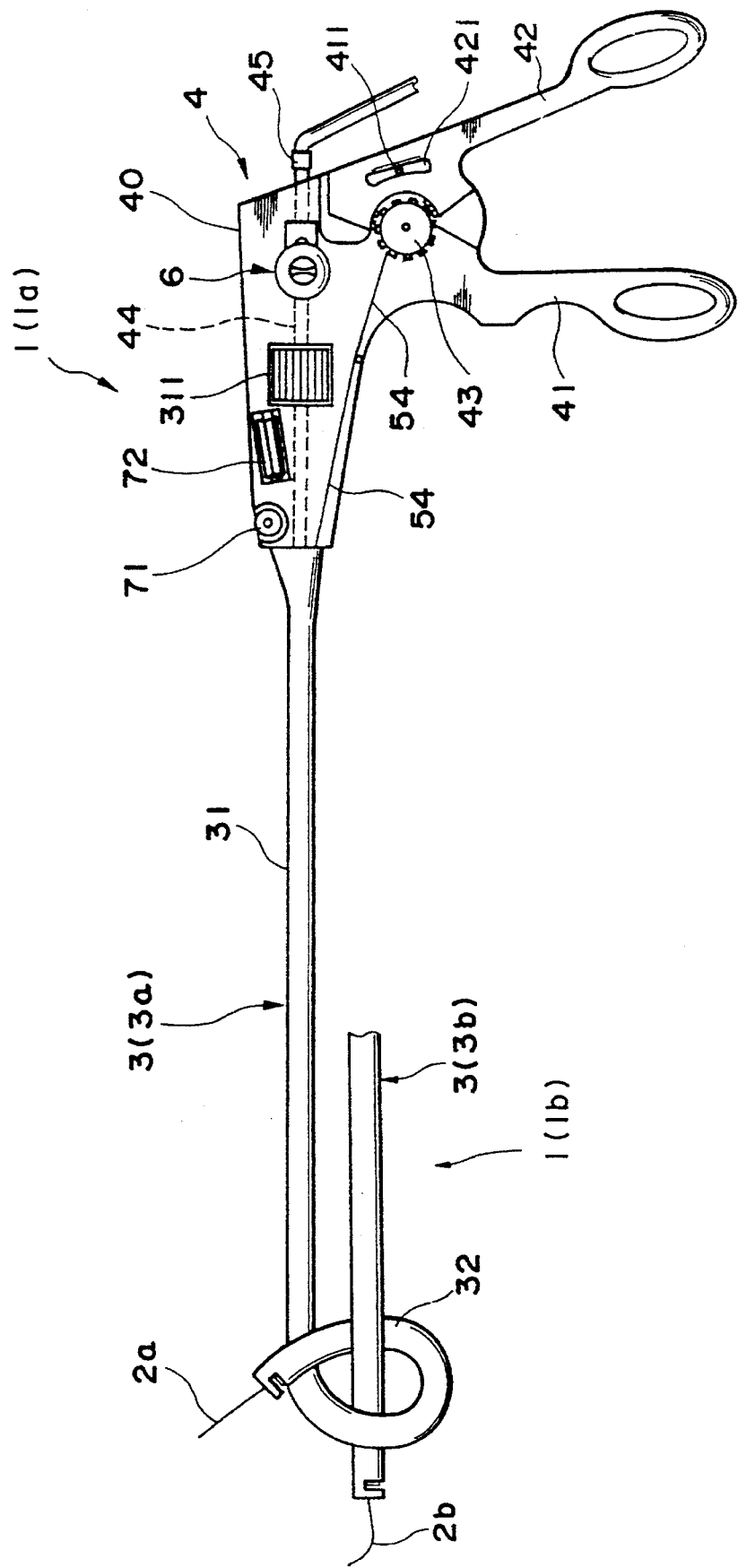
FIG. 1 is an entire side view showing a first embodiment of a knot forming instrument according to the present invention, in which a loop is formed at the tip portion thereof.

FIG. 1 shows an entire side view of a first embodiment of the knot-forming instrument according to the present invention. In this drawing, the tip portion of a control rod 3 is shown in a state of being inclined about 90 degrees relative to the control apparatus 4.

The knot-forming instrument 1 of the first embodiment of the present invention comprises the control rod 3 and a control apparatus 4 for remote controlling the control rod 3 from the outside of the body. The control rod 3 has a tip portion, and the tip portion is adapted to be inserted into the inside of the body cavity through a trocar tube (not shown in the drawings). The trocar tube is positioned to pass through the abdominal wall and acts as a communicating tube for communicating the outside of a body with one portion of the inside of the body cavity.

Figure 2:
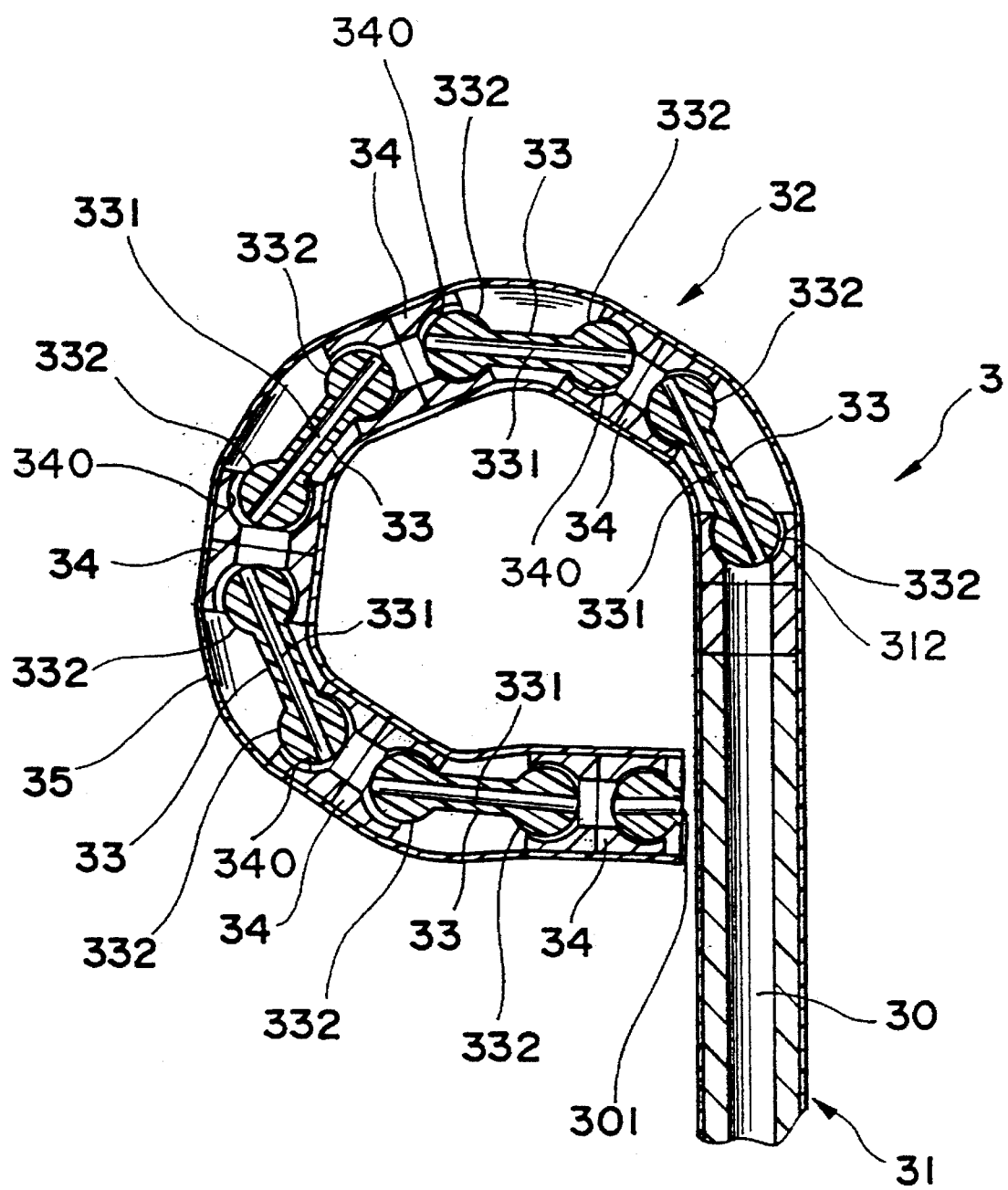
FIG. 2 is a cross sectional view showing the internal structure of a bendable portion of the instrument.

The control rod 3 has a substantially straight portion 31 and a bendable portion 32 formed on the substantially tip portion thereof. A base end portion of the straight portion 31 is connected to a main body 40 of the control apparatus 4 so as to be freely rotatable thereto. The base end portion is provided with a large diameter portion 311 of which the outer circumferential surface partially protrudes from both sides of the main body 40. By rotating the large diameter portion 311 by hand, it is possible to rotate the control rod 3. And as shown in FIG. 2, an insertion path 30 is formed inside the substantially straight portion 31 along its axial direction.

Figure 3:
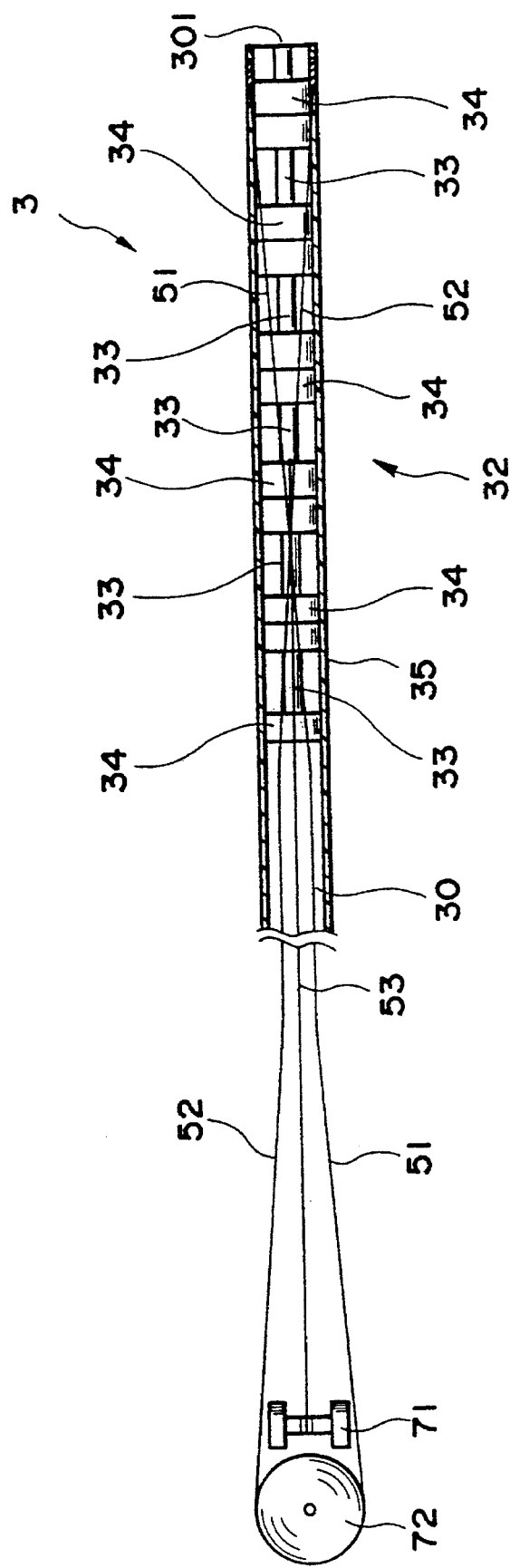
FIG. 3 is a cross sectional view showing the internal structure of the bendable portion, in which arrangement of wires are shown.

As shown in FIG. 3, wires 51, 52, 53 are provided so as to pass through the inside of the control rod 3 for adjusting the bending state of the bendable portion 32 to be described hereinbelow. In addition to these wires, there is a wire 54 provided so as to pass through a lower side of the control rod 3 for controlling a cutting means. The wires may be constructed from reinforced threads, metal or the like, but for the purpose of providing a preferable bendability for the bendable portion 32 without increasing a rigidity thereof, it is preferable to utilize reinforced threads.

As for the bendable portion 32, it is connected to the tip end of the substantially straight portion 31. As shown in FIG. 2, the bendable portion 32 has tube bodies 33 which are a plurality of unit members and ring-shaped coupling members 34 for operatively connecting the tube bodies 33. Each tube body 33 has an insertion passage 331 that passes through the tube body 33 along the axial direction thereof, and opposite end portions 332. Both end portions 332 of each tube body 33 are formed so as to have a spherical shape, respectively. The coupling members 34 are positioned between the tube bodies 33 so as to receive the spherically-shaped end portions 332 of the adjacent tube bodies which are opposed to each other, within both end portions of the coupling members 34. The inner surface of each of the both end portions of the ring-shaped coupling member 34 is formed into a spherically-shaped concave surface to which the spherically-shaped end portion of the tube body can be pivotally fitted.

In this embodiment, the tip end portion of the substantially straight portion 31 is formed with a connection opening 312 with the bendable portion 32. This connection opening 312 is formed with a concave spherically-shaped portion that receives the end portion 332 of the tube body 33 located at the base end of the bendable portion 32. As the end portions 332 of the tube bodies 33 are in slidable contact with the coupling members 34, they are able to pivot freely thereabout. Namely, as there are spherically shaped connecting surfaces between the tube bodies 33 and the coupling members 34, there is no particular limit with regards to the direction in which the tube bodies 33 can pivot relative to the coupling members 34.

Accordingly, as the tube bodies 33 are coupled to the coupling members 34 by means of the spherical joints described above, it becomes possible to bend the entire bendable portion 32 in a roughly continuous manner. This makes it possible to bend the bendable portion 32 by any degree of curvature in any direction desired.

The outer circumferences of the coupling members 34 are covered by a flexible covering member 35. Also, in order to facilitate easy movement of the wires, it is preferable to apply a lubricant such as silicone, grease or the like to the outer surface of the wires or the inside surface of the covering member 35.

As for the insertion path 30, a portion thereof is formed by the insertion passages 331 of each tube body 33 and the inner cavities of each coupling member 34. At the tip end of the insertion path 30, namely, at the tip end of the bendable portion portion 32, there is an opening 301 that forms the opening of the control rod 3.

With the above construction, the bendable portion 32 can be substantially straightened or bent with any degree of curvature.

Now, as shown in FIG. 3, the ends of the wires 51, 52 are fixed to the tip portion of the control rod 3 at opposite positions as viewed in the cross section thereof (in this embodiment, at the the left and right portions of the cross sectional view). The wires 51, 52 are wound around each of the coupling members 34 of the bendable portion 32 and pass along the inside surface of the covering member 35. Further, in the vicinity of the base end portion of the bendable portion 32, these wires 51, 52 reach the positions which are opposite to the positions where the wires 51, 52 are fixed when viewed in the cross section thereof, and further pass through the inside of the straight portion 31 parallel to the axis thereof. Moreover, even though it is not illustrated in the figures, it is also possible to form grooves in the outer surface of the coupling members 34 for smoothly guiding the motion of each wire.

As for the wire 53, it is fixed in an upper portion of the bendable portion 32, as viewed in the front of the cross-sectional drawing, so as to pass through the inside of the bendable portion 32 along the axis thereof. The wire 53 is arranged in the direction of the axis of the bendable portion 32 and its tip end is fixed at the position which is far away from the center to a position near the base end thereof.

By pulling the wires 51, 52, 53 described in the arrangement above, it is possible to control the shape of the bendable portion 32. If either wire 51 or 52 is pulled, the bendable portion 32 will be bent in the direction of the wire pulled, which allows a deformation into an α-shaped configuration. At this time, since the wires 51, 52 pass through the inside of the control rod 3 under the condition that they are wrapped around the coupling members 34 of the bendable portion 32, this causes the bendable portion 32 to bend spirally to form a single loop.

Figure 4:
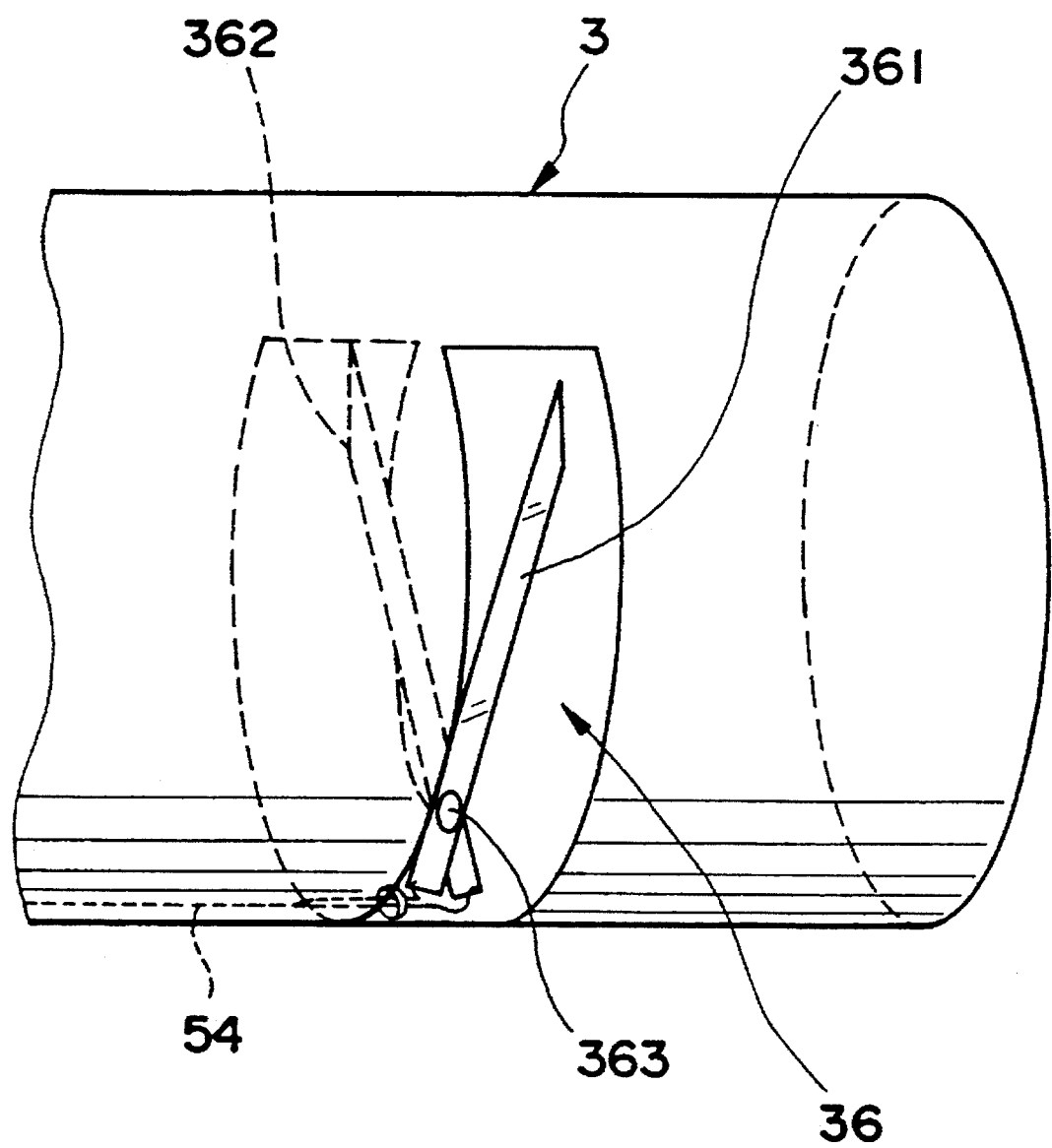
FIG. 4 is transparent perspective view showing the structure of a cutting means, in which a mounting position of scissors and the structure thereof are illustrated.
Figure 5:
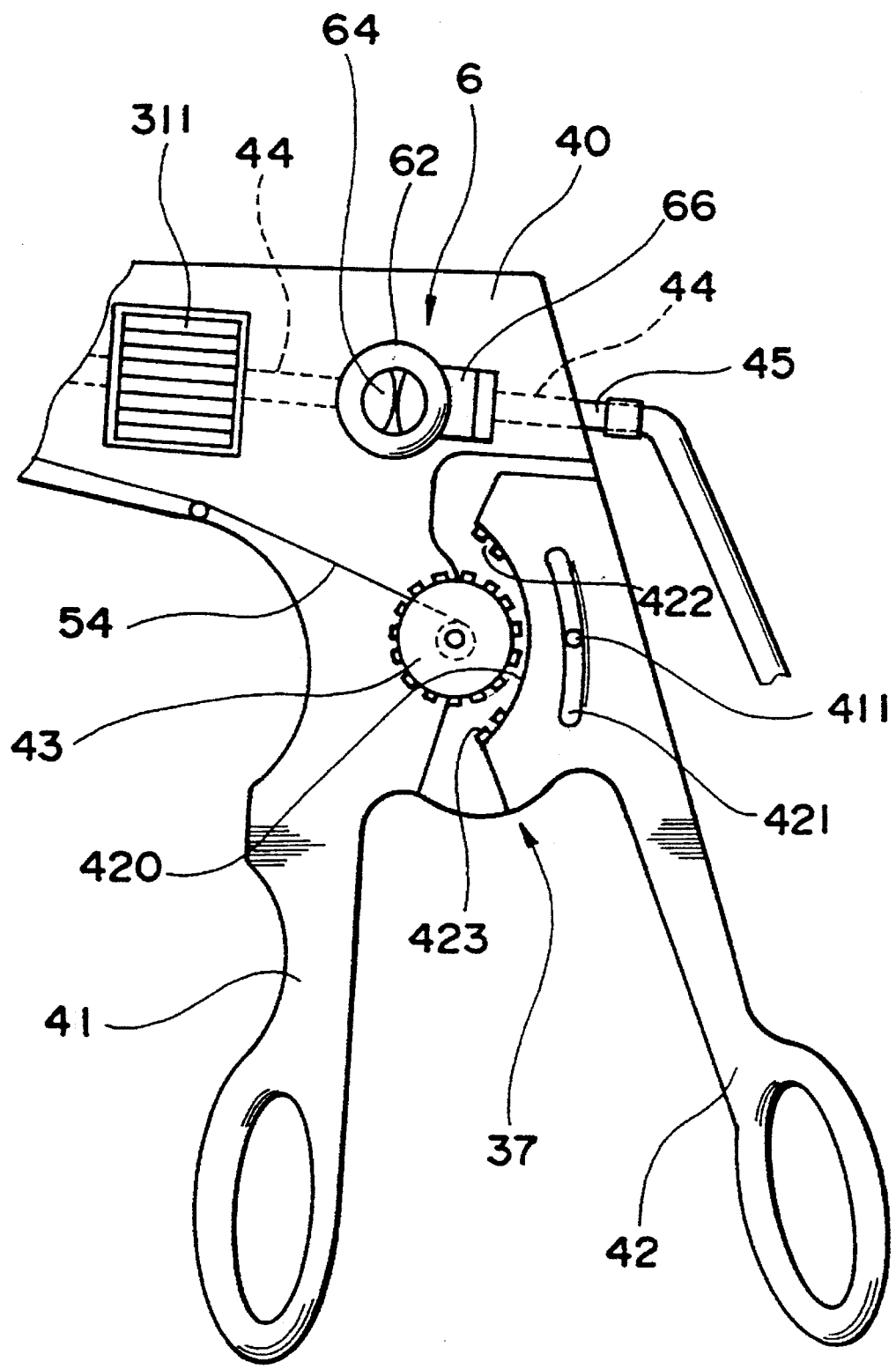
FIG. 5 is a side view of a portion of a control device, in which the structure of a control section of the cutting means is illustrated.

The bendable portion 32 is further provided with a cutting means for cutting threads at the tip portion thereof. As shown in FIGS. 4 and 5, the cutting means comprises scissors 36 and a handle 37 for controlling the operation of the scissors 36. The scissors 36 are constructed from a pair of blades 361, 362. Each of these blades 361, 362 may be formed into an arced shape so as to conform with the vertical cross-sectional shape of the bendable portion. The blades 361, 362 pivot around a pivot point 363, and the tip end of the wire 54 is connected to the base ends of the blades 361, 362, respectively. In order to connect the wire 54 to the base ends of the blades 361, 362, it is bifurcated into two segments, in which each segment being connected to the respective base end of the blades 361, 362. In the vicinity of the scissors 36, the two bifurcated segments of the wire 54 are bundled together to form a single strand. Accordingly, when the wire 54 is pulled, the bifurcated section thereof pulls upon the base ends of the blades 361, 362 to cause them to come together. Then, by the provision of a spring means (not shown in the drawings), when the wire 54 is slackened, the blades will be caused to return to their open position.

In the above construction, the diameter of the control rod is such as to be insertable through a trocar tube, for example 3–5 mm. For laparoscopic surgeries, the length of the control tube is preferably around 350–400 mm long, but can be made to vary depending upon such factors as the part of the body to be operated on, the body type of the patient, age of the patient and the like.

As for the length of the bendable portion 32, it is preferred to lie in the range of 30–50 mm. If the length is smaller than this, the size of the loop will be so small that it will become difficult to pass a thread through the loop in order to form a knot. If the length is bigger than this, the size of the loop becomes large and this can lead to difficulties when operating in relatively small spaces within the body cavity.

The control device 4 has a mechanism for pulling wires 51, 52, 53, 54, and a tension means for holding a thread that is inserted through the insertion path 30 and for maintaining a proper tension on the thread at all times. The control device 4 is also connected to an aspirating means for pulling the thread into the insertion path 30.

At a lower portion of the main body 40 of the control device 4, there is a fixed handle portion 41, and attached near a base portion of the handle portion 41 is a movable handle portion 42 which is freely pivotable thereto. At the base portion of the fixed handle portion 41 near the movable handle portion 42, there is an axially supported winding gear 43. The winding gear 43 forms a winding axis (not shown in the drawings) for winding the wire 54, and by operating the handle (to be described hereinbelow) and thereby rotating the winding gear 43, the wire 54 is wound around the axis and therefore pulled to operate the cutting means 36.

In the movable handle portion 42, there is formed a slit 421 that runs in the direction from top to bottom, and inside the slit 421 there is inserted a pin 411. The pin 411 is provided so as to rise up from the main body 40 and acts as the pivotal support point for the movable handle portion 42. The movable handle portion 42 pivots around the pin 411, and by changing the position of the pin 411 in the slit 421 by moving the movable handle portion 42, it is possible to change the pivotal point for the movable handle portion 42.

Furthermore, the movable handle portion 42 has a curve-shaped contact surface 420 that faces and follows the circumferential surface of the winding gear 43, and formed at the top and bottom end portions of the contact surface 420 are gear teeth portions 422, 423 which are engageable with the winding gear 43. In this way, a handle means 37 is constructed from the fixed handle portion 41, the movable handle portion 42 and the winding gear 43 for pulling the wire 54 in order to operate the cutting means 36.

Next, the operation of the handle means 37 will be described.

When the movable handle portion 42 is slid downwardly, the pin 411 becomes positioned in the upward direction of the slit 421 and the movable handle portion 42 pivots in the direction so as to open the fixed handle portion 41 and the movable handle portion 42, and this causes the gear teeth portion 422 to engage with the winding gear 43. Next, by moving the movable handle portion 42 further in the direction of opening of the fixed handle portion 41 and the movable handle portion 42, the gear teeth portion 422 causes the winding gear 43 to rotate in the counterclockwise direction with respect to the drawings, and this slackens the wire 54. By carrying out this operation, the scissors provided at the end portion of the control rod 3 are caused to open.

When the scissors 36 are to be closed in order to cut the thread, the movable handle portion 42 is first slid upwardly to position the pin 411 in the lower portion of the slit 421, and then the movable handle portion 42 is pivoted in the direction to close the fixed handle portion 41 and the movable handle portion 42, which causes the gear teeth portion 423 to engage with the winding gear 43. Next, by moving the movable handle portion 42 further in the direction of closing the fixed handle portion 41 and the movable handle portion 42, the gear teeth portion 423 causes the winding gear 43 to rotate in the clockwise direction with respect to the drawings, and this causes the wire 54 to be wound on the winding gear 43. As a result, the wire 54 is pulled to close the scissors 36 to cut the thread that is passed through the insertion path 30. Thus, the use of the handle means 37 makes it possible to cut the thread with a scissor action that feels the same as that for a standard pair of scissors.

In the main body 40, there is provided a passage 44 that is connected at one end thereof with the insertion path 30 of the control rod 3 connected to the main body 40. At the other end of the passage 44, there is an opening formed in the back portion of the main body 40, and connected to this opening is an aspirating nozzle 45 which is connected to an aspirating apparatus (not shown in the drawings) for drawing or pulling a thread.

When the aspirating apparatus is activated to bring about an aspirating force in the aspirating nozzle, a negative pressure is generated inside the passage 40 and the insertion path 30, which causes a thread to be sucked into the opening 301 of the control rod 3 to be guided through the inside of the insertion path 30 and the passage 44.

As for the aspirating apparatus, in addition to the use of motorized equipment, it is also possible to utilize constructions employing such things as rubber balloons or bellows and a check valve and the like, and it is possible to construct these aspirating means to be operated by hand.

Figure 6:
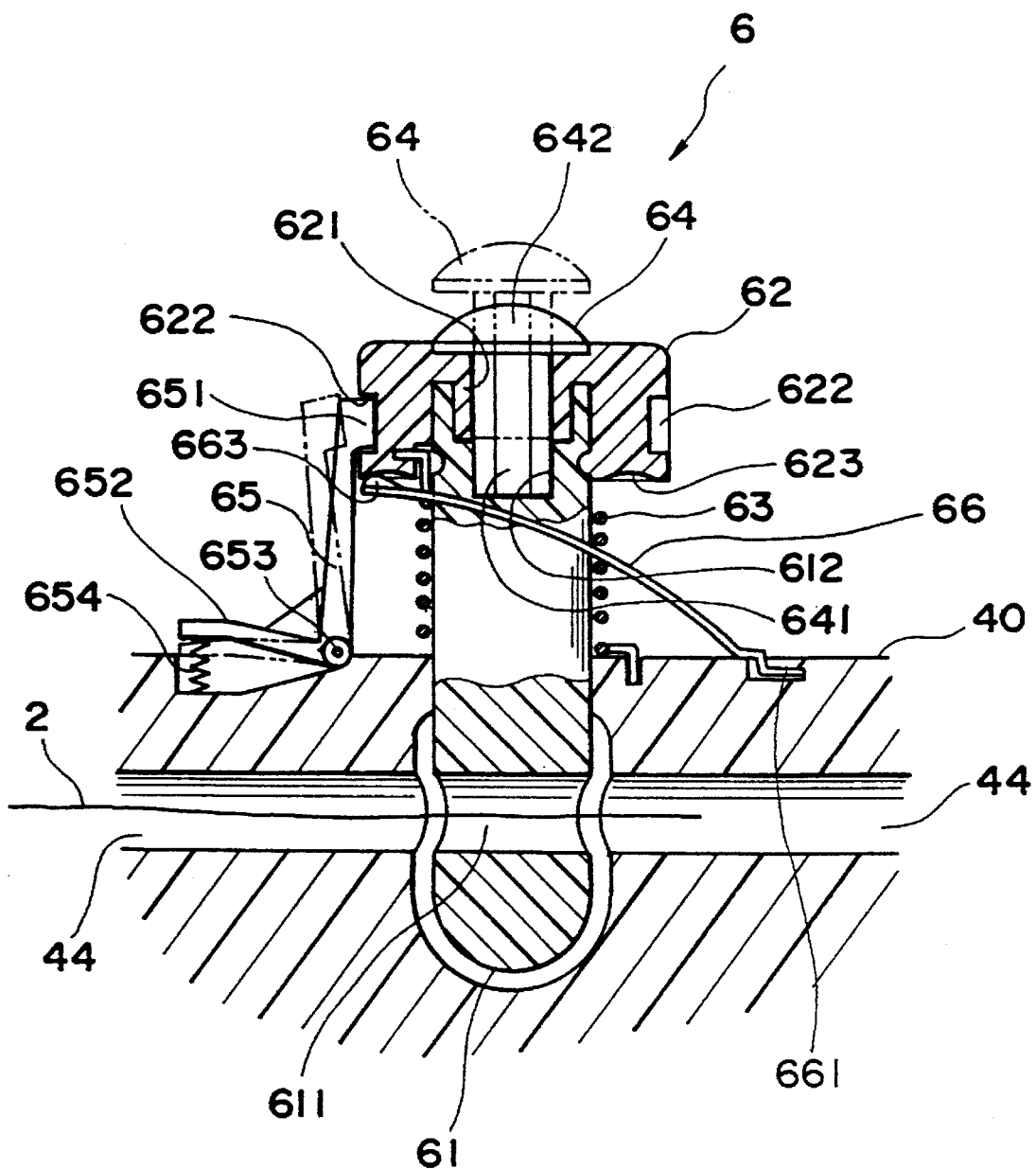
FIG. 6 is a sectional side view of a winding mechanism.

In the passage 44 in the space between the aspirating nozzle 45 and the base portion of the insertion path 30 of the control rod 3, there is provided a winding mechanism 6 that acts as a tensioning means. FIG. 6 is a cross-sectional side view showing an example of the winding mechanism 6.

As shown in FIG. 6, the winding mechanism 6 comprises a winding axis 61 that is freely rotatably connected to the main body 40 and is inserted into the passage 44 so as to block the passage 44, a rotatable knob 62 that is freely rotatably fitted to the top end of the winding axis 61, a biasing spring 63 wound around the winding axis 61 for applying the biasing force to the winding axis 61 in a certain direction of rotation of the winding axis 61, a connecting member 64 that connects the rotatable knob 62 and the axis 61 so as to form a single rotatable body, and a locking member 65 for preventing the rotatable knob 62 from being rotated by the biasing force of the spring 63.

Formed in the winding axis 61 is an aperture 611 having a diameter roughly the same size as that of the passage 44, and by rotating the winding axis 61 it is possible to either align the aperture 611 with the passage 44 (aspirating condition) or to completely disconnect the aperture 611 and the passage 44 (non-aspirating condition). It should be noted here that it is also possible to carry out the drawing of a thread by directly connecting the aspirating apparatus. Since any hospitals have equipment such as the aspirating apparatus, the use of the aspirating apparatus as the thread introducing means would be convenient.

Formed in a portion of the axis 61 that protrudes outside the main body 40 is a substantially regular hexagonal shaped hole 612, which is covered by the rotatable knob 62 in a freely rotatable manner.

In the center of the rotatable knob 62, there is formed a hole 621 having substantially the same regular hexagonal shape as the hole 612, and removably inserted into the holes 612 and 621 is the connecting member 64. The connecting member has a substantially regular hexagonal shaped rod portion 641, which has substantially the same cross-sectional shape as the holes 612 and 621, and the rod portion 641 has a knob portion 642 at one end thereof. By inserting this connecting member 64 through the holes 612 and 621, the rotatable knob 62 and the winding axis 61 are able to rotate as a single body. As shown by the two positions of the connecting member 64 in FIG. 6, by removing the connecting member 64 from the hole 612 such that the rod portion 641 is disengaged from the hole 612, the rotatable knob 62 is able to rotate freely with respect to the winding axis 61, thereby making it possible for the rotatable knob 62 to either rotate freely with respect to the winding axis 61 or to rotate together with the winding axis 61 as a single body.

Figure 7:
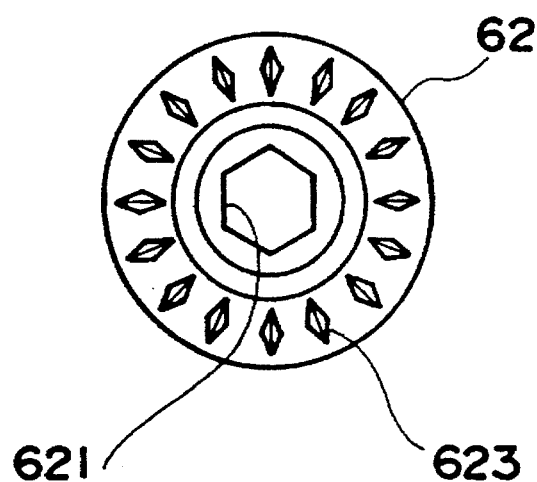
FIG. 7 is a bottom view of a rotation knob of the winding mechanism.

As for the spring 63 that surrounds the winding axis 61, one end thereof abuts the main body 40 and the other end abuts the rotatable knob 62. Consequently, when the rotatable knob 62 is rotated in one direction, the biasing force of the spring acts In the opposite direction. In this state, when the connecting member 64 is pushed to connect the rotatable knob 62 and the winding axis 61, the biasing force of the spring 63 causes the winding axis 61 to rotate, thereby winding the thread. Furthermore, as shown in FIG. 7, formed in a bottom portion of the rotatable knob 62 following the circumference thereof are a series of equally spaced concave portions 623, and formed in the outer circumference of the rotatable knob 62 are a plurality of equally spaced noches 622 that are axially formed.

Provided in the vicinity of the winding axis 61 is the locking member 65. At an upper end portion of the locking member 65, an engaging portion 651 is formed for engaging any one of the notches 622 of the rotatable knob 62, and at a base end portion of the locking member 65 there is formed an L-shaped arm portion 652. At the arm portion 652 there is an axial support portion 653 that allows the locking member 65 to pivot freely with respect to the main body 40. Inserted between an end portion of the arm portion 652 and the main body 40 is a biasing member 654 that acts to bias the arm portion 652 away from the main body 40. In this way, the normal state of the engaging portion 651 is biased to engage any one of the notches 622 of the rotatable knob 62. Thus, when the engaging portion 651 is engaged with any one of the notches 622 of the rotatable knob 62, the rotatable knob 62 is prevented from rotating.

When the locking member 65 is to be released to allow the rotatable knob 62 to rotate, the end portion of the arm portion 652 is pushed down towards the main body 40. This results in the locking member 65 pivoting so as to disengage the engaging portion 651 from the notch 622, which unlocks the rotatable knob 62 for rotation to be carried out.

Figure 8:
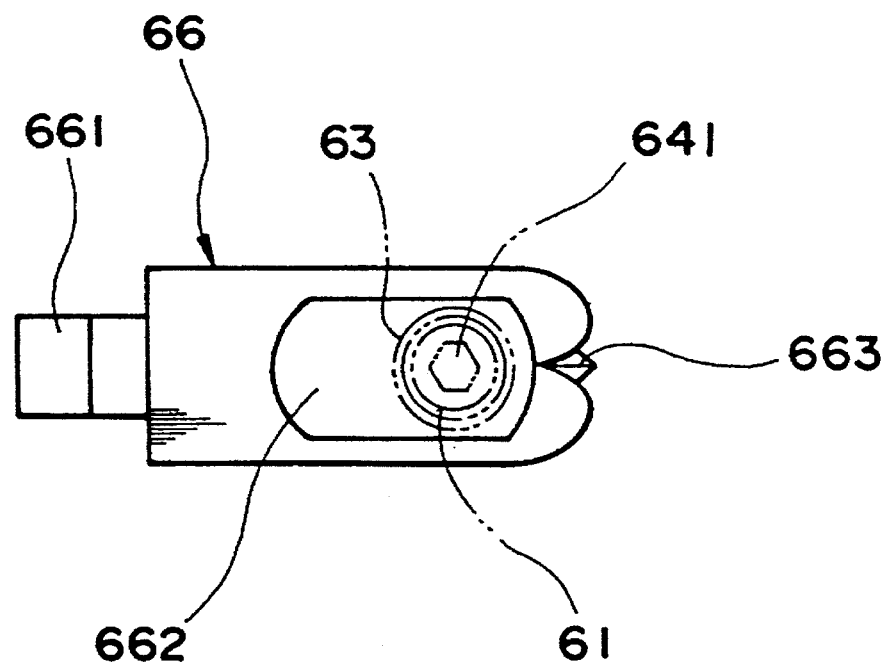
FIG. 8 is a plan view of a leaf spring of the winding mechanism.

Facing the winding axis 61 is a plate spring 66 that is fixed on the side opposite the position where the locking member 65 is provided. As shown in FIG. 8, the plate spring 66 has a fixed end in order to be fixed to the main body 40, a hole 662 through which the winding axis 61 is inserted, and a convex portion 663 formed on the end opposite to the fixed end 661. Due to the elastic force of the spring 66, the convex portion 663 makes contact with any one of the concave portions 623 formed in the bottom surface of the rotatable knob 62. A rotation regulating means for suppressing or reducing the rotation of the winding axis 61 is composed of the plate spring 66, the convex portion 663 and the concave portion 623.

When the rotatable knob 62 is rotated, the convex portion 663 of the plate spring 66 gradually engages with any one of the concave portions 623 of the rotatable knob 62. When the rotatable knob 62 and the winding axis 61 are rotated by means of the biasing force of the spring 63, the engagement of the convex portion 663 of the plate spring 66 with any one of the concave portions 623 of the rotatable knob 62 allows for a gentle winding to take place by preventing the winding axis 61 from accelerating beyond a predetermined rate of rotation.

When a thread 2 is to be wound, the thread 2 is pulled into the hole 611 of the winding axis 61 by means of the thread introducing means of the aspirating means, and while in this state the winding axis 61 is rotated. This then causes the thread 2 inside the hole 611 to be wound around the winding axis 61.

Described next will be the operation of a bending motion control mechanism 7 for operating the bendable portion 32 of the control rod 3. As shown in FIG. 1 and FIG. 3, in the vicinity of the connecting portion that connects the control rod 3 to the main body 40, a winding reel 71 and a pulling reel 72 are axially supported on the main body 40 and are provided so as to be freely rotatable thereto.

The wire 53 is wrapped around the winding reel 71, and when the wire 53 is wound therearound, the wire 53 is pulled to cause the bendable portion 32 to bend in the upward direction. In this case, the winding reel 71 is rotated by rotating the circumferential surface with fingers.

As for the winding reel 71, it is possible to replace the reel with other means for pulling the wire 53, such as a control lever or a manual operation by hand or the like, thereby enabling the bendable portion 32 to be bent.

Wrapped in opposite directions around the pulling reel 72 are the wires 51, 52. Accordingly, when the pulling reel 72 is rotated in one direction, one of the wires 51, 52 is pulled and the other is slackened, so that when the bendable portion 32 is bent by the wire that is pulled, the other wire is slackened to prevent any disturbance of the bending operation.

Furthermore, when the winding reel 71 is rotated, the wire 53 is pulled, and this causes the loop formed by the bendable portion 32 to incline with respect to the straight portion 31 of the control rod 3. In this way, by inclining the loop, it makes it easier to pass the thread through the loop.

Now, an example of a knot-forming method using the knot-forming instrument of the present invention having the above-described construction will be described with reference to FIGS. 9 and 10. First, a plurality of trocar tubes are inserted through the abdominal wall to act as communicating tubes that communicate the outside of the body with the inside of the body cavity, and in this method two knot-forming instruments 1a, 1b are employed.

As seen in the drawings, two threads 2a, 2b are seen in a state after they have passed through body tissue, for example, after they have been used to suture body tissue by a suturing instrument passed through one of the other trocar tubes. In this case, the thread 2a, 2b may be two separate threads or both ends of a thread.

The knot-forming instruments are inserted into the body cavity by passing control rods 3a, 3b with their bendable portions in a straight condition through different trocar tubes. In a manner similar to that described above, when the movable knob 62 and the connecting portion 64 are manipulated, the winding mechanism 6 is operated. At this time, by activating the aspirating means, a strand 2a of the suturing thread 2 that has been passed through body tissue is sucked inside the end of the control rod 3a of the knot-forming instrument 1a, and is then securely held and wound by the winding mechanism 6. After the strand 2a has been wound, the locking member 65 is used to lock the winding mechanism 6 against further movement.

By rotating the pulling reel 72 of the knot-forming instrument 1a in a prescribed direction, the bendable portion 32 is bent so as to form an g-shaped loop. Next, the winding reel 71 is rotated to wind the wire 53, which then sets the thus-formed loop in a position that is inclined relative to the straight portion 31.

Next, as shown in FIG. 1, while being maintained in a straight condition, the end of the other knot-forming instrument 1b is passed through the inside of the loop-shaped bendable portion 32. In this state, the aspirating means is employed to suck a strand 2b of the suturing thread 2 into the tip end of the control rod 3b to be held securely by the winding mechanism 6.

Figure 9A:
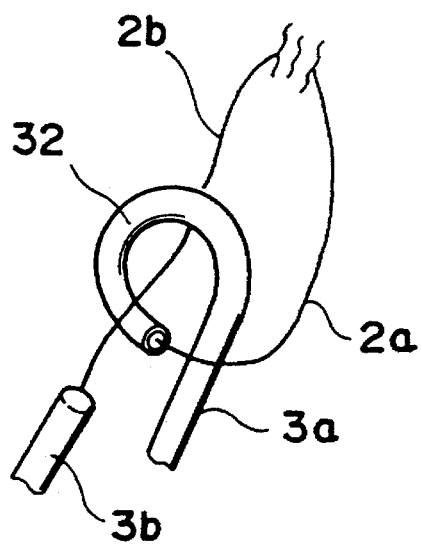
FIGS. 9A to 9D are enlarged perspective views of the tip portion of the control rod, which illustrate steps for forming a first knot by utilizing the knot forming instrument according to the first embodiment.
Figure 9B:
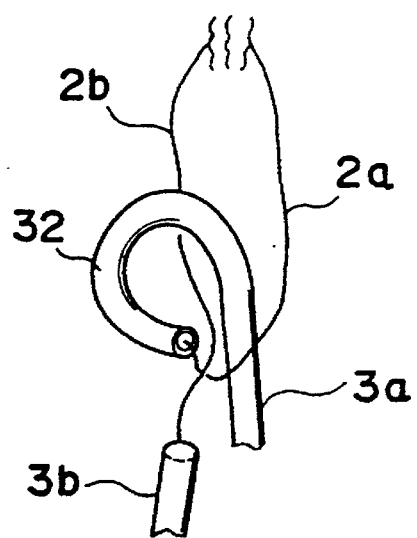
Figure 9C:
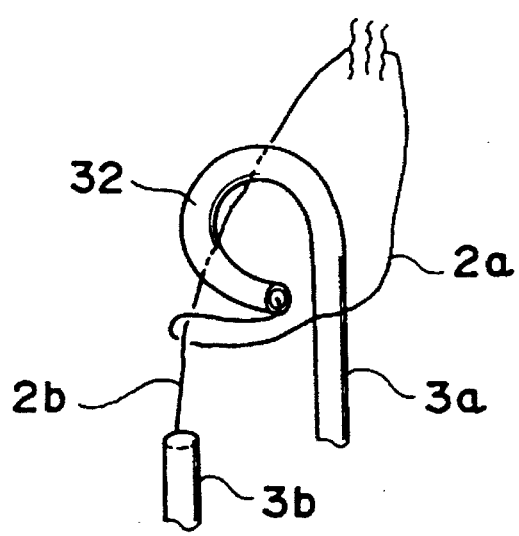
Figure 9D:
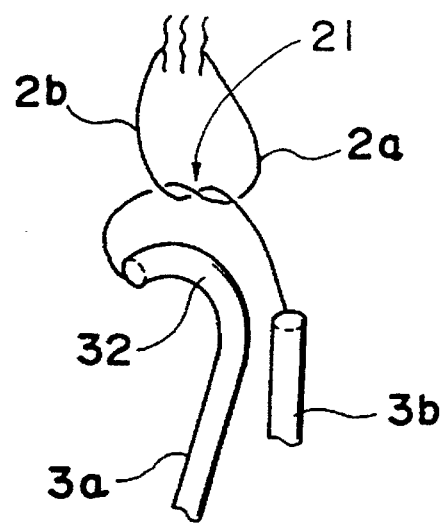

Then, as shown in FIG. 9A, by pulling the control rod 3b that has been inserted through the loop-shaped bendable portion 32, the strand 2b is caused to pass through the inside of the loop. Next, as shown in FIG. 9B, the control rod 3b is moved to cause the strand 2b to cross with the strand 2a in the vicinity of the end opening portion of the control rod 3a, and as shown in FIG. 9C, the control rod 3b is further moved to push the intersection of the strands 2a and 2b to the outside of the loop. Finally, as shown in FIG. 9D, the strands 2a and 2b are twisted to form a single knot 21. In this case, these operations can be performed by moving or rotating the control rod 3a by which the loop is formed.

Next, for securing the knotted thread 2 to the tissue being sutured, the tensioning means of the knot-forming instrument 1a and/or 1b is operated. For example, when using the tension means of both the knot-forming instruments 1a, 1b, the tip end portions thereof are returned to a straight condition and the locking members 65 and 65 are released to permit rotation of the respective knobs 62 and 62, which then allows the biasing force of the springs 63 and 63 to rotate the respective winding axes 61 and 61, thus resulting in the strands 2a and 2b being wound in a controlled manner. This winding of the strands 2a, 2b causes the tip ends of the control rods 3a, 3b to move towards the tissue being sutured, and this results in the knot 21 being tightened against the tissue to enable the forming of a secure knot.

Now, when performing ligations and the like during surgery, it is preferable to form a second knot 22 having an inverted twist so as to make it difficult that the first knot 21 undone. To accomplish this, both locking members 65, 65 are released and the axes 61, 61 are then rotated in the opposite direction while the control rods 3a, 3b are pulled back away from the first knot 21 in order to provide enough slack for the strands 2a, 2b to enable the forming of the second knot 22.

Next, the winding axis 61 of the knot-forming instrument 1b is further reversed to establish the state depicted in FIG. 6. Namely, the strand 2b that has been pulled inside the control rod 3b is released to the outside for example by blowing air through the aspirating nozzle 45 into passage 44 to create a positive pressure that acts to push the strand 2b back out of the control rod 3b.

Figure 10A:
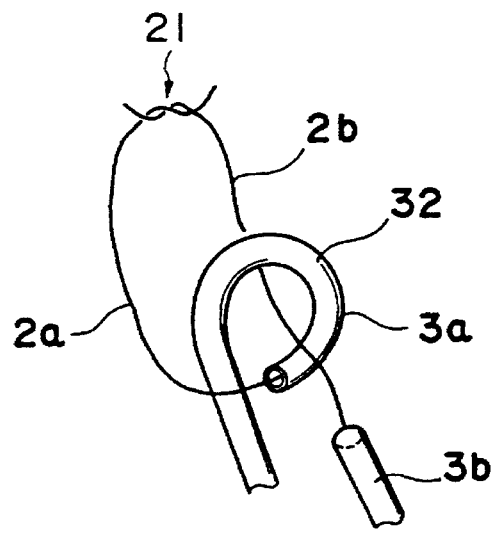
FIGS. 10A to 10D are enlarged perspective views of the tip portion of the control rod, which illustrate steps for forming a second knot by utilizing the knot forming instrument according to the first embodiment.
Figure 10B:
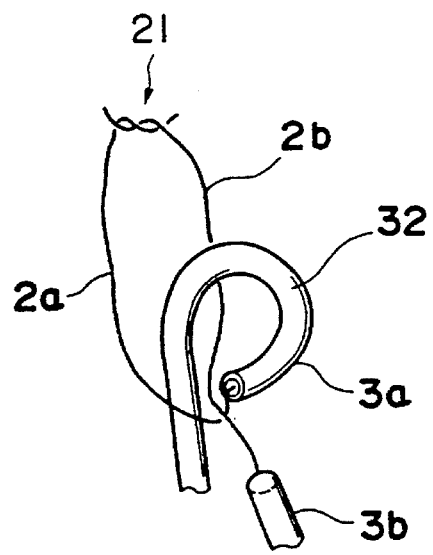
Figure 10C:
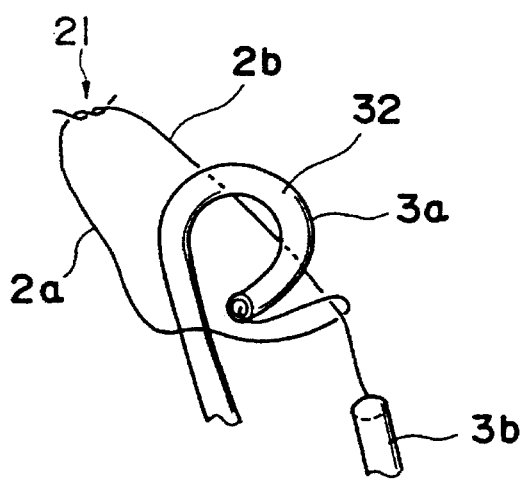
Figure 10D:
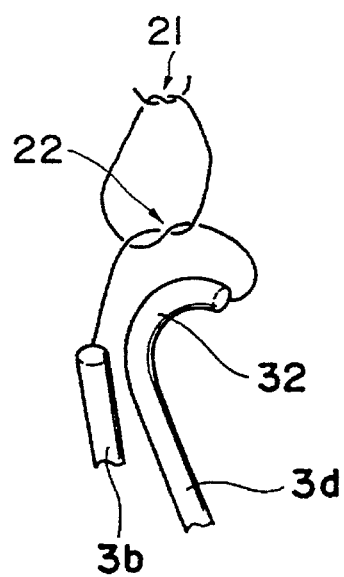

Now, the control rod 3a of the knot-forming instrument 1a forms another loop along a curve path that is the mirror image of the curved path used for forming the loop used in making the first knot 21, and this mirror-image loop is formed around the tip end of control rod 3b so that the strand 2b passed therethrough, as shown in FIG. 10A. Thereafter, the strand 2b which has been released or discharged from the control rod 3b is aspirated again by the control rod 3, and then the tip end of the control rod 3b is pulled back to be positioned out of the loop. Then, as shown in FIGS. 10B to 10D, the same steps as were performed for forming the first knot 21 (FIGS. 9B to 9D) are repeated to form the second knot 22. This second knot 22 is then pulled tautly against the first knot 21 in order to secure the two knots 21, 22 together against the tissue being sutured.

Once the above steps have been completed, the suturing procedure is finished by operating the movable handles 42, 42 of the knot-forming instruments 1a, 1b and by rotating the winding gears 43, 43 thereof to pull their respective wires 54 to operate scissors 36, 36 to cut the strands 2a, 2b.

In forming the second knot 22, it is possible to carry out the above procedure by either pushing the strand 2a out of the control rod 3a and then using the aspirating means to draw it back in again, or pushing both strands 2a, 2b out of their respective control rods 3a, 3b and then using the aspirating means to draw the strands 2a, 2b back in again. Alternatively, it is possible to carry out the above-described procedure by forming a loop with the control rod 3b instead of the control rod 3a and then passing the control rod 3a in a straight condition through the loop to form the knot.

According to the above described method, it is possible to easily carry out suturing, ligations and the like in a short time with ease. Furthermore, as the suturing thread is wound automatically, it is possible for one practitioner to perform the procedure using his or her right and left hands to operate, respectively, the knot-forming instruments 1a, 1b. Moreover, as opposed to the problems arising from the use of staple-like means, the above described procedure involves the use of suturing threads, which makes it possible to carry out safe and reliable suturing, ligation, anastomosis and the like.

Figure 11:
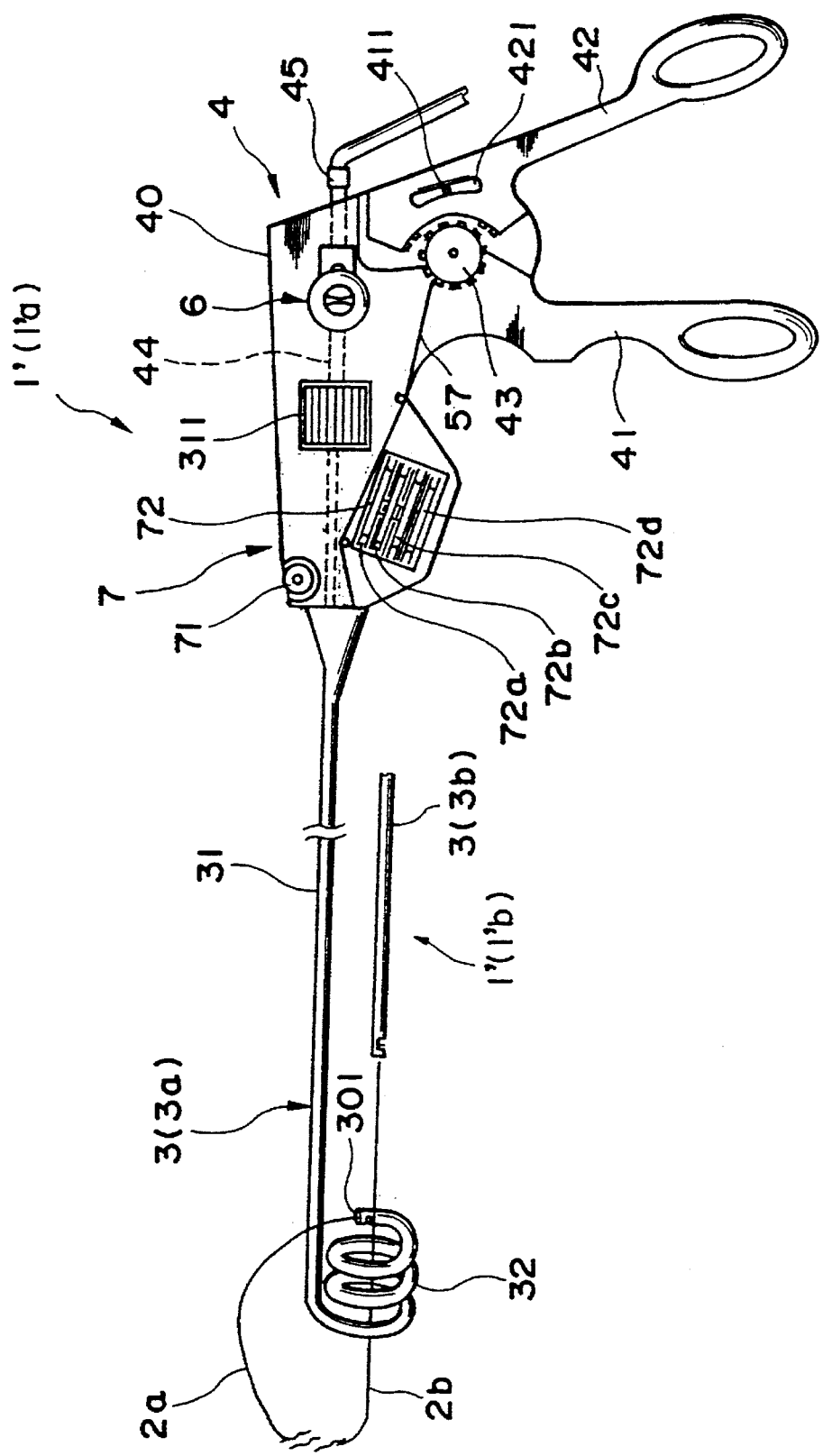
FIG. 11 is an entire side view showing a second embodiment of a knot forming instrument according to the present invention, in which a helical loop is formed at the tip portion thereof.

Next, a second embodiment of a knot-forming instrument according to the present invention will be described. In this regard, FIG. 11 shows a complete side view of a second embodiment of a knot-forming instrument according to the present invention. As shown in FIG. 11, the tip of a control rod 3 is shown in a state of being inclined 180 degrees relative to the control apparatus 4. Now, in the description given below for the second embodiment, the same reference marks and characters that were used in the first embodiment will be used to indicate the same elements and components, and therefore a detailed description of such elements will be omitted.

The knot-forming instrument 1' of the second embodiment of the present invention comprises a control rod 3 having a tip end portion for reaching the inside of the body cavity and a control apparatus 4 for remote controlling the control rod 3 from the outside of the body. The tip portion of the control rod 3 is inserted through a trocar tube (not shown in the drawings) that acts as a communicating tube for communicating the outside of a body with one portion of the inside of the body cavity by being positioned to pass through the abdominal wall. As in the case of the first embodiment, the control rod 3 has a substantially straight portion 31 and a bendable portion 32.

Figure 12:
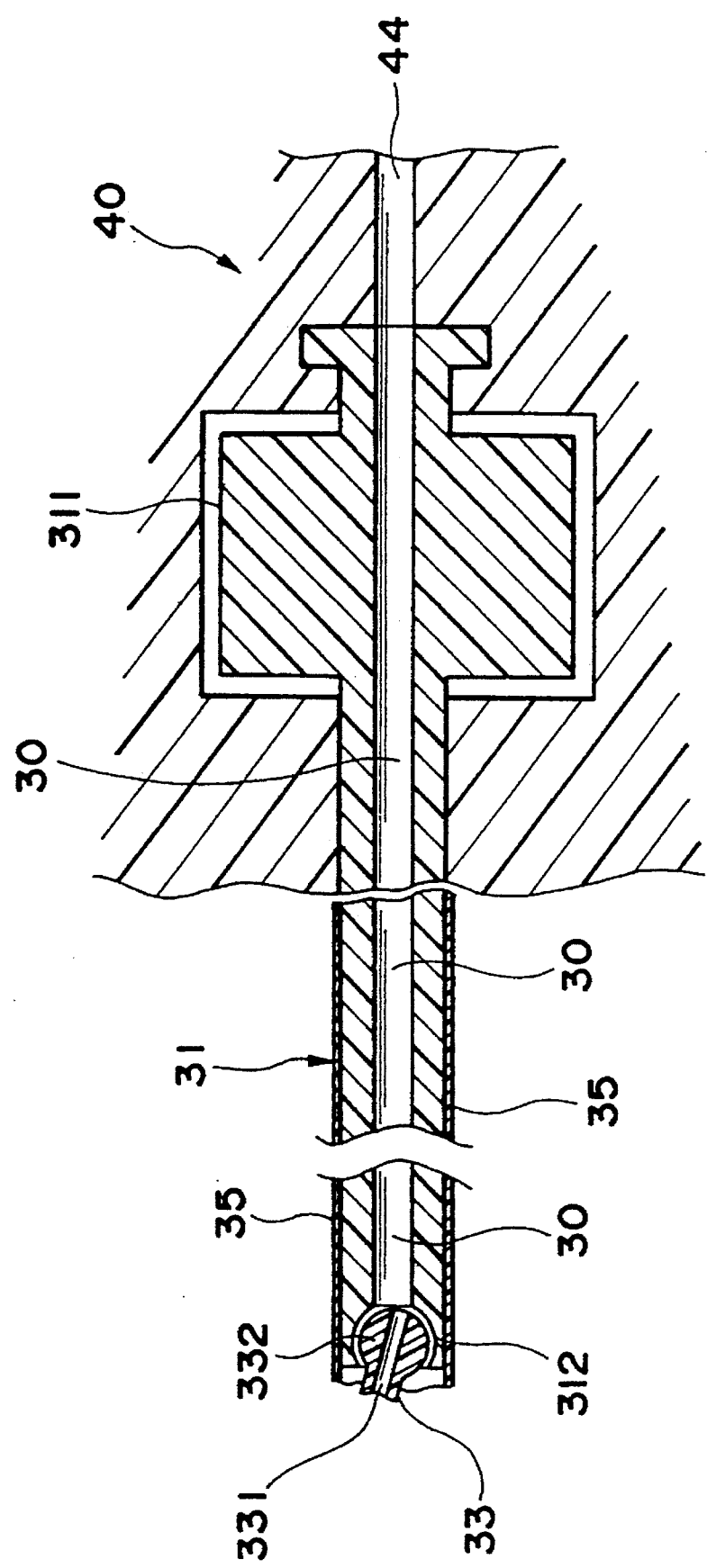
FIG. 12 is a partial cross sectional view showing an internal structure of a straight portion of a control rod.
Figure 13:
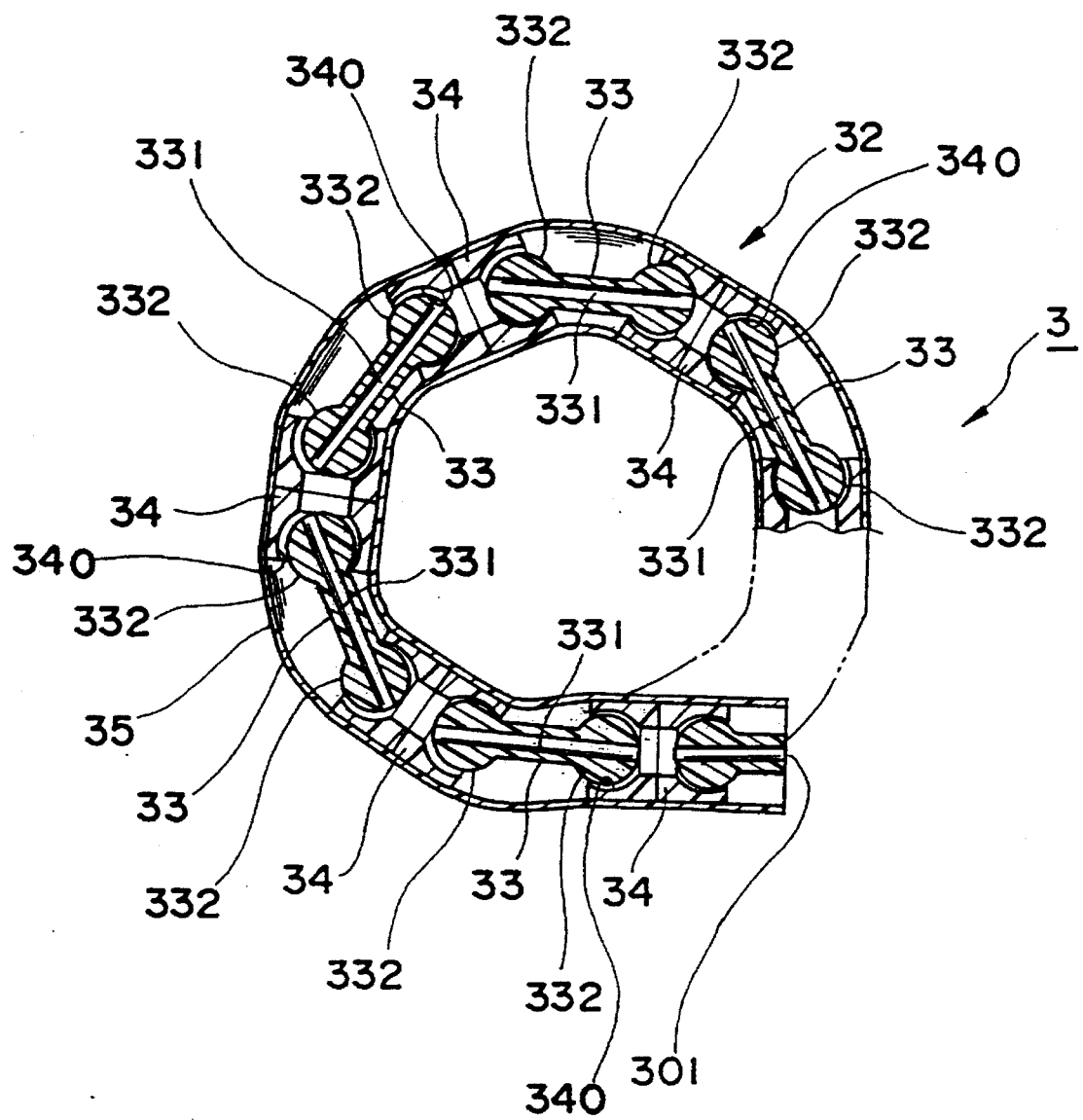
FIG. 13 is a cross sectional view showing the internal structure of a bendable portion of the instrument.

As shown in FIG. 12, the tip end portion of the straight portion 31 is formed with a connection opening 312 at the connection point with the bendable portion 32. This connection opening 312 is formed with a concave spherically-shaped portion that receives the end portion 332 of the tube body 33 located at the base end of the bendable portion 32. As the end portions 332 of the tube bodies 33 are in slidable contact with the coupling members 34, they are able to pivot freely thereabout. As shown in FIG. 13, the bendable portion 32 of the second embodiment of the knot-forming instrument of the present invention has the same construction as the bendable portion of the first embodiment, and is therefore able to bend in the same manner.

Figure 14:
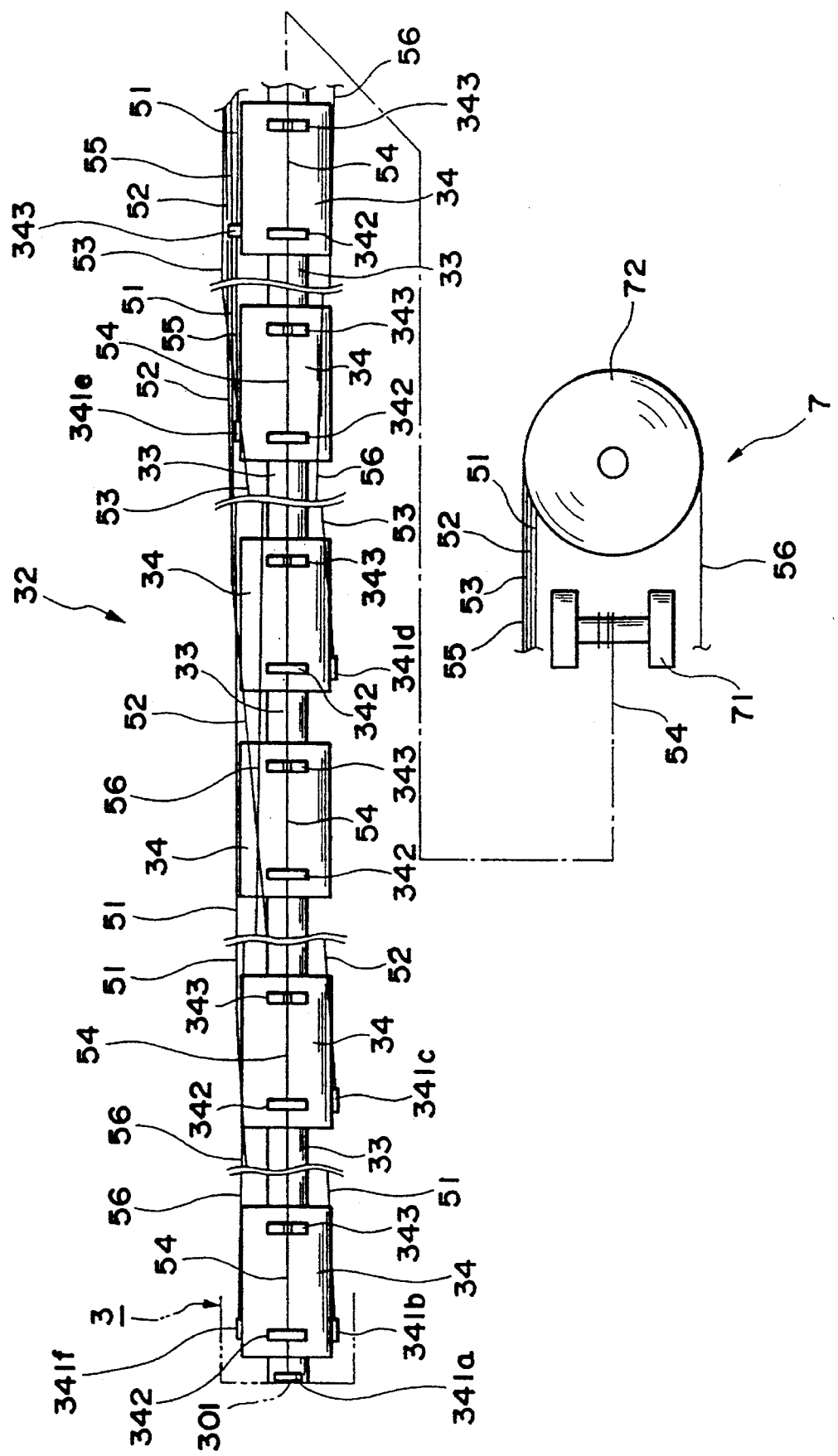
FIG. 14 is a transparent top plan view of the control rod for explaining the arrangement of wires passing therethrough.

Now, as shown in FIG. 14, alternately provided on the coupling members 34 of the bendable portion 32 are lower guide portions 342 and upper guide portions 343 for guiding the wire 54. Formed in a base portion of the respective lower guides 342 in the axial direction of the coupling members 34 are holes, and through these holes is passed the wire 54. Furthermore, the wire 54 is also passed through a groove formed in an upper portion of the respective upper guides 343 along the axial direction of the coupling members 34.

As is also shown in FIG. 14, wires 51, 52, 53, 54, 55, 56, and 57 are provided so as to pass through the inside of the control rod 3 for adjusting the bending condition of the bendable portion 32 and for operating the cutting means.

Figure 15:
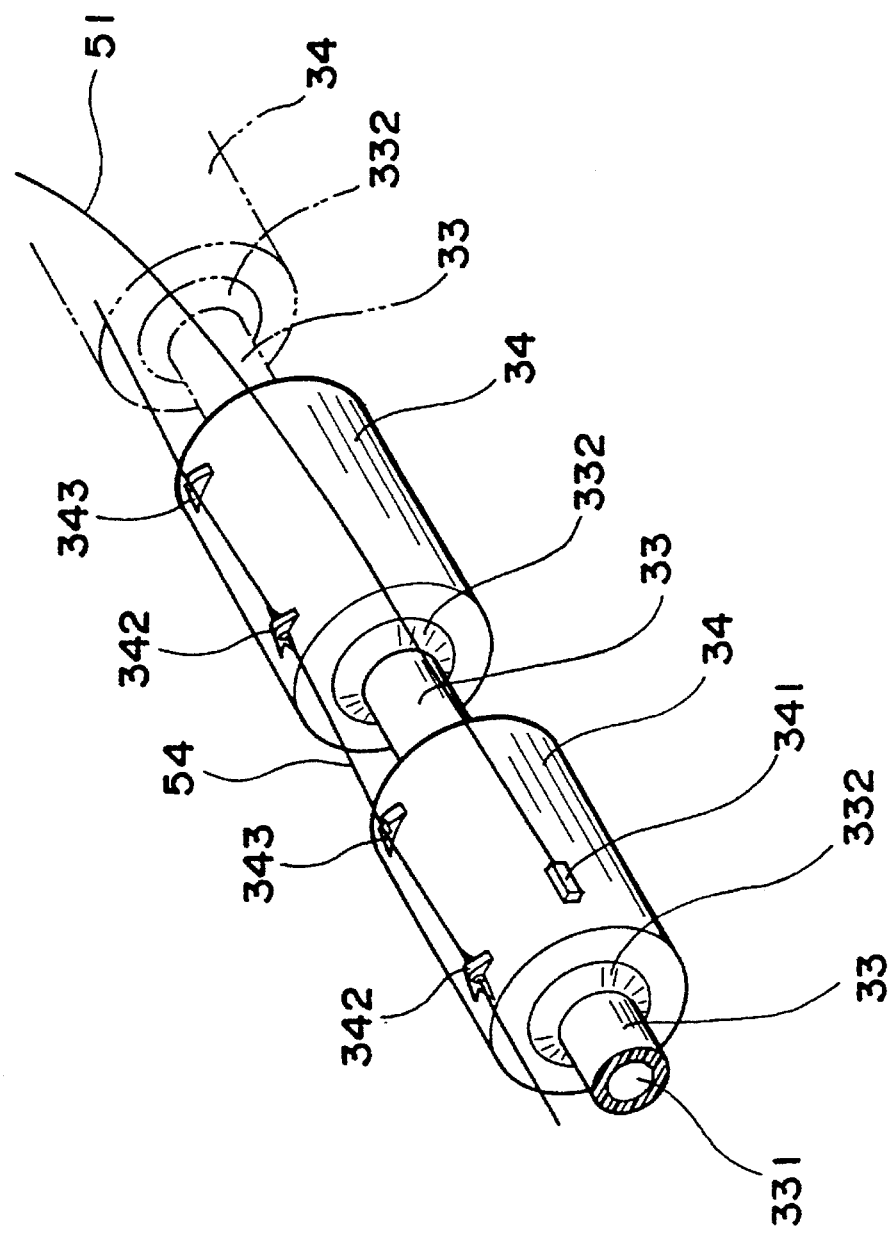
FIG. 15 is a transparent perspective view of the bendable portion for explaining the arrangement of wires passing therethrough.

FIGS. 14 and 15 show the arrangement of the wires 51, 52, 53, 54, 55, 56. Wires 51, 52, 53 and 54 are used to bend the bendable portion 32 into a spiral-shaped loop (coil); wire 55 is used to control the direction of spiral-shaped loop formed by the bendable portion 32; and wire 56 is used to return the bendable portion 32 from a bent state to its original state. The arrangement of these wires will now be explained below.

One tip end of the wire 54 is fixed to a fixing portion 341a located at the tip end of the bendable portion 32, and the wire 54 is alternatively passed through the lower guide portions 342 and the upper guide portions 343 of the connecting members 34 so as to follow along the axis of the control rod 3, and the other end of the wire 54 is wound around the winding reel 7 provided in the main body 40 of the control apparatus 4. As shown in FIG. 15, as the wire 54 passes through the lower guide portions 342 and the upper guide portions 343 alternately, it alternately bends up and down. By the arrangement of the lower guide portions 342 and the upper guide portions 343, it is possible to increase the extent to which the bendable portion 32 can be bent.

Thus, by operating the winding reel 71, the wire 54 is pulled and wound, the bending portion 32 is bent within the same plane, and the wire is further pulled, the bendable portion 32 will be further bent and wrapped into a spiral form (in this embodiment, the bendable portion 32 can wrap around two and a half times).

As for the wire 51, the tip end thereof is fixed to a fixing portion 341b provided on the outer circumferential surface of the endmost coupling member 34, with the wire 51 being provided to follow along the outer circumferential surface of the bendable portion 32 so as to wrap therearound, while the base end of the wire 51 is wound around a reel 72a provided in the main body 40 of the control device 4. The length of the bendable portion 32 that is wrapped with the wire 51 is, in the present embodiment, about ⅓ the total length of the bendable portion 32, and the wrapped angle is about 180 degrees. In other words, when viewed in the cross section, the wire wraps from the fixing portion 341b to the opposite side of the bendable portion 32. The rest of the wire 51 is arranged to run parallel to the axis of the bendable portion 32 and the straight portion 31.

With the above arrangement, when the wire 51 is pulled, the bendable portion 32 is caused to twist, and this operation combines with the action of the wire 54 to cause the end portion of the control rod 3 to form a spiral loop (a single coil).

In a similar manner as that described above, the wire 52 is provided in essentially the same way as the wire 51. Namely, the tip end of the wire 52 is fixed at a fixing portion 341c located on the outer circumferential surface of the coupling member 34 where the wire 51 completes its wrap, and the wire 52 is in turn wrapped around the outer circumferential surface of the bendable portion 32. The base end of the wire 52 is wound around a reel 72b which is provided in the main body 40 of the control device 4.

Furthermore, the wire 53 is provided in essentially the same way as the wire 51. Namely, the tip end of the wire 53 is fixed at a fixing portion 341d located on the outer surface of the coupling member 34 where the wire 52 completes its wrap, and the wire 53 is in turn wrapped around the outer surface of the bendable portion 32. The base end of the wire 53 is wound around a reel 72c which is provided in the main body 40 of the control device 4.

By operating the wires 51, 52, and 53, the bendable portion 32 is caused to twist, and this operation combines with the action of the wire 54 to make it possible for the bending portion 32 of the control rod 3 to form a spiral loop (a coil).

As for the wire 55, the tip end thereof is fixed at a fixing portion 341e located on the outer circumferential surface of the coupling member 34 where the wire 53 completes its wrap, and from there the wire 55 is passed through the upper guide portion 343 provided at the base end of the bendable portion 32 and then follows along the axis of the control rod 3. The base end of the wire 55 is wound around a reel 72d which is provided in the main body 40 of the control device 4.

By operating the wire 55, as shown in FIG. 1, the spiral shaped loop formed with the bendable portion 32 can be made to bend at the base portion thereof so as to point the tip end portion toward the control device 4, and this makes the treatment by the instrument easy.

As for the wire 56, the tip end thereof is fixed at a fixing portion 341f provided at the tip end portion of the bendable portion 32. The fixing portion 341f, when viewed from a cross section of the control rod 3, is position on the opposite side of the control rod 3 with respect to the position where the fixing portion 341b is positioned. The wire 56 wraps around the bendable portion 32 as is passes along over roughly the entire length of the bendable portion 32, and as it does so, the wire 56 maintains a position that is on the opposite side of the bendable portion 32 to the positions of the wires 51, 52, and 53. Also, the wrapped angle of the wire 56 is about 180 degrees. Thus, by pulling the wire 56, it is possible to undo the loop and return the bendable portion 32 to a straight shape. Then by further pulling the wire 56, the bendable portion 32 can be made to form a single loop in the opposite direction.

The knot-forming instrument 1' is provided with the same type of cutting means as was provided for the knot-forming instrument 1 of the first embodiment. The cutting means of the knot-forming instrument 1 has the same construction as is shown in FIG. 6. Namely, the construction comprising scissors 36 and an operating handle 37 for operating the scissors 36. Moreover, the operation of the cutting means is carried out in the same way as described before. Namely, by manipulating the movable handle portion 42 of the operating handle 37, the winding gear 43 is caused to rotate, which in turn pulls the wire 57 to operate the scissors 36 to cut the thread.

As for the dimensions of the control rod 3 such as outer diameter, length and the like, it is preferable to use roughly the same dimensions as was used in the first embodiment. However, the length of the bendable portion 32 is preferably set to be in the range of 30–100 mm. If the length is smaller than this, the size of the loop will be so small that it will become difficult to pass a thread through the loop in order to form a knot. If the length is bigger than this, the size of the loop becomes large and this can lead to difficulties when operating in relatively small spaces within the body cavity.

The control device 4 has a mechanism for pulling wires 51, 52, 53, 54, 55, 56, 57 and the same tension means and aspirating means as was described above. Moreover, the mechanisms shown in FIGS. 6 to 8 are equally applicable to the knot-forming instrument 1' of the second embodiment.

Next, an explanation will be given below for a bending control mechanism 7 used for operating the bendable portion 32 of the control rod 3.

As shown in FIGS. 11 to 14, in the vicinity of the connecting portion that connects the control rod 3 to the main body 40, a winding reel 71 and a pulling reel 72 are axially supported on the main body 40 and are provided so as to be freely rotatable thereto in the same manner as the first embodiment. Thus, when the wire 54 is pulled by being wound around the winding reel 71, the bendable portion 32 is caused to bend in the upward direction.

As for the pulling reel 72, it is composed of reels 72a, 72b, 72c, 72d around which are wound, in the same direction, wires 51, 52, 53, 55, respectively. Furthermore, wire 56 is also wound around reel 72a, but is wound in the direction opposite to the direction that wire 51 is wound.

Accordingly, as the pulling reel 72 is rotated so that the reels 72a, 72b, 72c, 72d rotate together, for example, in the clockwise direction with respect to FIG. 14, the wires 51, 52, 53, 55 are pulled and the wire 56 is slackened. At this time the pulling of the wires 51, 52, 53, 55 causes the bendable portion 32 to bend, and since the wire 56 is slackened, the wire 56 does not cause any hindrance to the bending of the bendable portion 32. Here it is to be noted that it is also possible to construct the reels 72a, 72b, 72c, 72d to have different diameters to permit different rates of pull for their respective wires 51, 52, 53, 55.

Furthermore, when the winding reel 71 is rotated, the wire 54 is pulled and this causes the end of the spiral-shaped loop formed by the bendable portion 32 to bend towards the control device 4, and this makes it easier to pass the thread through the loop.

Now, an example of a knot-forming method using a knot-forming instrument 1' according to the second embodiment of the present invention having the above-described construction will be described with reference to FIGS. 16 and 17. In this example, a plurality of trocar tubes are inserted through the abdominal wall, which act as communicating tubes for communicating the outside of the body with the inside of the body cavity, and in this arrangement two knot-forming instruments 1' are employed. As seen in the drawings, two threads 2a, 2b are seen in a state after they have passed through body tissue, for example, after they have been used to suture body tissue by a suturing instrument passed through one of the other trocar tubes.

The knot-forming instruments 1' are inserted into the body cavity by passing control rods 3a, 3b with their bendable portions in a straight condition through different trocar tubes. In a manner similar to that described above, when the rotatable knob 62 and the connecting member 64 are manipulated, the winding mechanism 6 is operated. At this time, by activating the aspirating means, a strand 2a of the suturing thread 2 that has been passed through body tissue is sucked inside the tip end of the control rod 3a of the knot-forming instrument 1'a, and is then securely held and wound by the winding mechanism 6. After the strand 2a has been wound, the locking member 65 is used to lock the winding mechanism 6 against further movement.

Now, when the winding reel 71 of the knot-forming instrument 1' is rotated and the wire 54 is wound therearound, the loop that has been formed is deformed into a coil-shaped loop that roughly lies within the same plane.

Then, when the pulling reel 72 is rotated, the coil-shaped loop is stretched along its axis of rotation to form a spiral-shaped (coiled) loop, and the base end of the bendable portion 32 bends in a way that causes the tip portion thereof to face toward the control device 4 (as shown in FIG. 11).

Next, as shown in FIG. 11, while being maintained in a straight condition, the tip end of the other knot-forming instrument 1b is passed through the inside of the spiral loop-shaped bendable portion 32. In this state the aspirating means is employed to suck the other strand 2b of the suturing thread 2 into the end of the control rod 3b to be held securely by the winding mechanism 6.

Figure 16A:
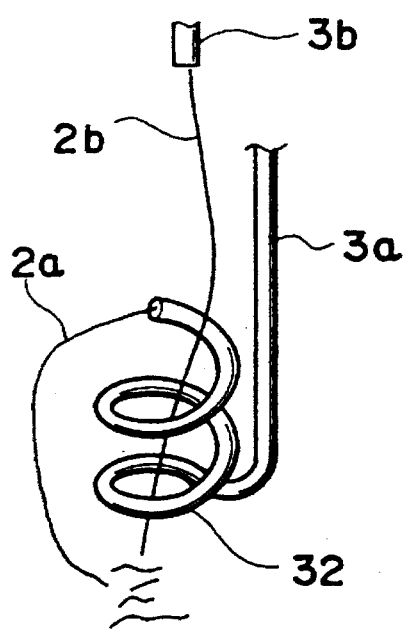
FIGS. 16A to 16D are enlarged perspective views of the tip portion of the control rod, which illustrate steps for forming a knot by utilizing the knot forming instrument according to the second embodiment.
Figure 16B:
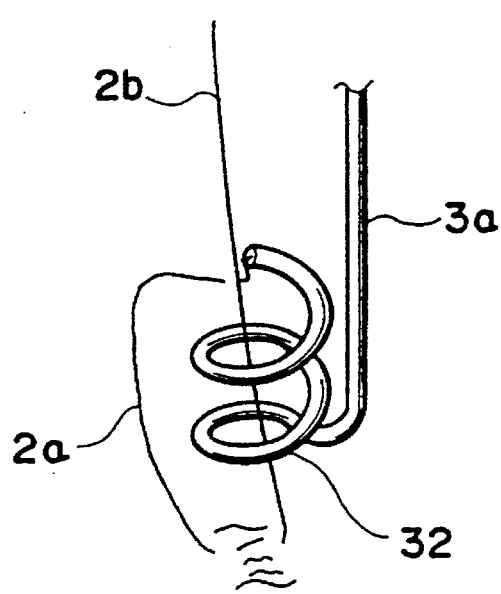
Figure 16C:
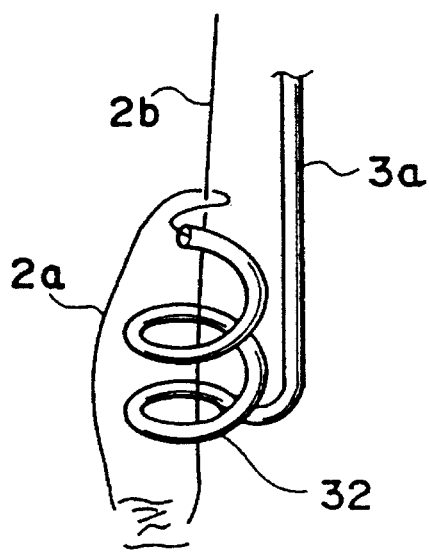
Figure 16D:
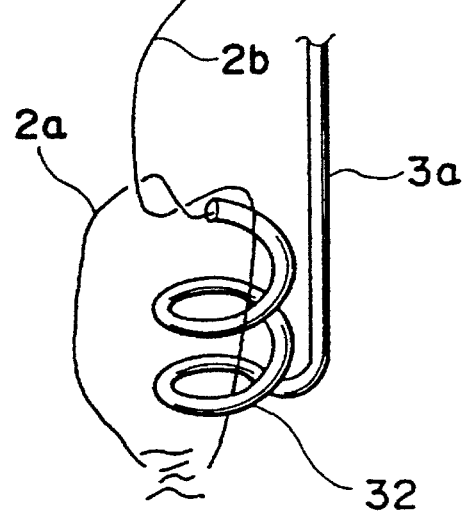
Figure 17A:
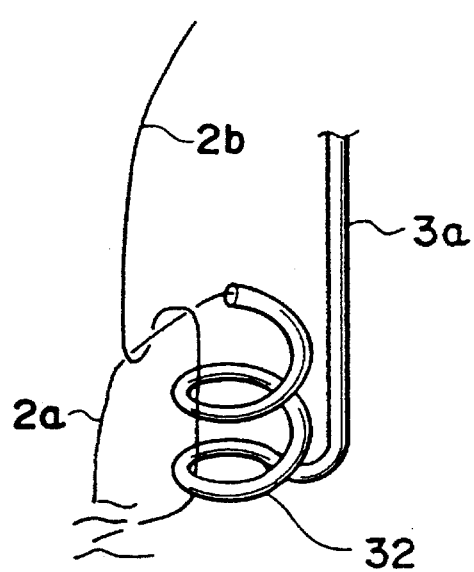
FIGS. 17A to 17C are enlarged perspective views of the tip portion of the control rod, which illustrate steps for forming the knot by utilizing the knot forming instrument according to the second embodiment.
Figure 17B:
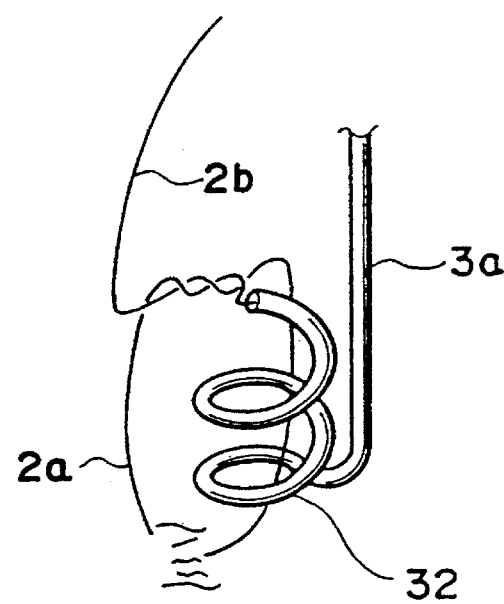
Figure 17C:
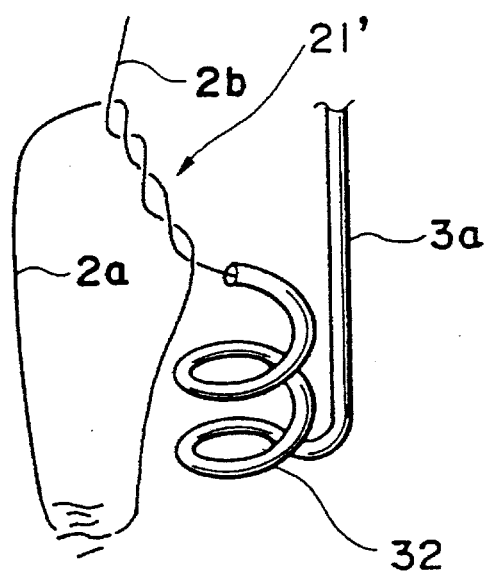

Then, as shown in FIG. 16A, by pulling the control rod 3b that has been inserted through the loop-shaped bendable portion 32, the strand 2b is caused to pass through the inside of the loop. Next, as shown in FIGS. 16B and 16C, the control rod 3b is moved to cause the strand 2b to cross with the strand 2a in the vicinity of the end opening portion of the control rod 3a, and as shown in FIG. 16D, the control rod 3b is further moved to push the intersection of the strands 2a and 2b to the outside of the first coil of the spiral-shaped loop. As a result, as shown in FIGS. 16D and 17A, the strands 2a and 2b are crossed to form a single knot in the same manner as the first embodiment. Finally, as shown in FIGS. 17A to 17C, the control rod 3b is manipulated still more to move the strand 2b around the second coil so as to move the strand 2b completely out of the spiral-shaped loop, and this results in the strands being twisted still more to form a double knot 21' as shown in FIG. 17C. Alternatively, it is possible to manipulate the control rod 3a, namely, the control rod by which the spiral-shaped loop of is formed, to obtain the same type of knot.

Next, for securing the knotted thread 2 to the tissue being sutured, the tensioning means of the knot-forming instrument 1'a and/or 1'b is operated. For example, when using the tension means of both the knot-forming instruments 1'a and 1'b, the tip end portions of the control rod 3a and 3b are returned to a straight condition and the locking members 65 and 65 are released to permit rotation of the respective knobs 62 and 62, which then allows the biasing force of the springs 63 and 63 to rotate the respective winding axes 61 and 61, thus resulting in the strands 2a and 2b being wound in a controlled manner. This winding of the strands 2a, 2b causes the tip ends of the control rods 3a, 3b to move towards the tissue being sutured, and this results in the knot 21' being tightened against the tissue to enable the forming of a secure knot.

Now, for reasons that were previously explained, it is necessary to form a second knot 22 having an inverted twist so as to prevent the first knot 21' from coming undone. To accomplish this, both locking members 65, 65 are released and the axes 61, 61 of the knot-forming instruments 1'a, 1'b are then rotated in the opposite direction while the control rods 3a, 3b are pulled back away from the first knot 21' in order to provide enough slack for the strands 2a, 2b to enable the forming of the second knot 22.

Next, the winding axis 61 of the knot-forming instrument 1'b is further reversed to establish the state depicted in FIG. 6. Namely, the strand 2b that has been pulled inside the control rod 3b is released to the outside by blowing air through the aspirating nozzle 45 into passage 44 to create a positive pressure that acts to push the strand 2b back out of the control rod 3b.

Figure 18A:
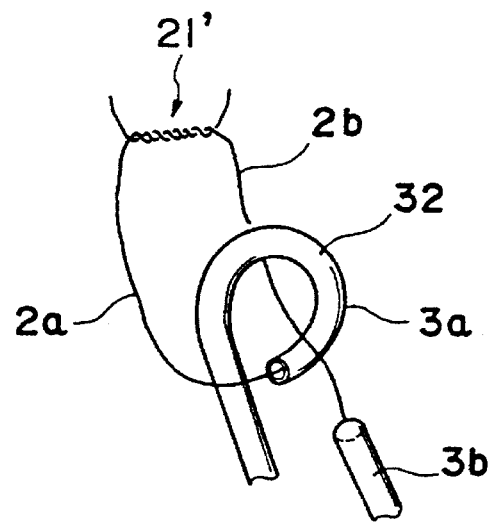
FIGS. 18A to 18D are enlarged perspective views of the tip portion of the control rod, which illustrate steps for forming a second knot by utilizing the knot forming instrument according to the second embodiment.
Figure 18B:
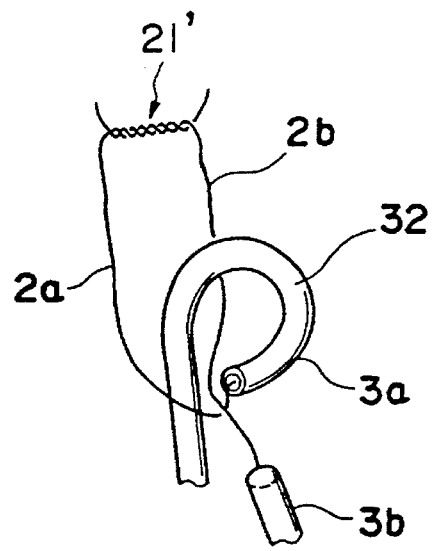
Figure 18C:
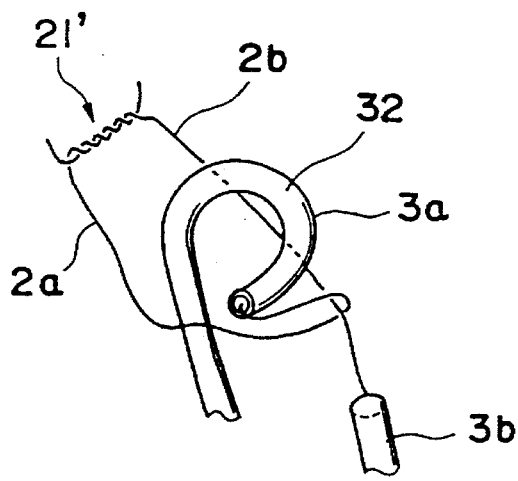
Figure 18D:
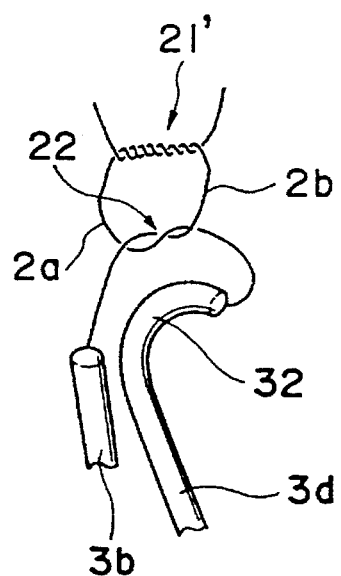

Now, the pulling reel 72 is rotated in the opposite direction to cause the bendable portion 32 of the knot-forming instrument 1'a to form a single coil loop along a path that curves in the opposite direction to the curved path followed by the spiral-shaped loop used in making the first knot 21', and through this single coil loop is passed the tip end of the control rod 3b so that the strand 2b passes therethrough. Thereafter, as shown in FIG. 18A, the released strand 2b is aspirated again from the tip end of the control rod 3b by utilizing the aspiration means, and then the control rod 3b is removed from the loop. This condition is shown in FIG. 18A. In this state, the strands 2a, 2b are securely held by the winding mechanisms 6, 6 of the knot forming instruments 1'a, 1b. Then, as shown in FIGS. 18B to 18D, the same steps as were performed for forming the second knot 22 (FIGS. 9B to 9D) for the example of the first embodiment are repeated to form the second knot 22' of this example. This second knot 22 is then pulled tautly against the first knot 21' in order to secure the two knots 21', 22 together against the tissue being sutured.

Once the above steps have been completed, the suturing procedure is finished by operating the movable handle portions 42, 42 of the knot-forming instruments 1'a, 1'b and thereby rotating the winding gears 43, 43 thereof to pull their respective wires 57 to operate scissors 36, 36 to cut the strands 2a, 2b.

In forming the second knot 22, it is possible to carry out the above procedure by either pushing the strand 2a out of the control rod 3a and then using the aspirating means to draw it back in again, or pushing both strands 2a, 2b out of their respective control rods 3a, 3b and then using the aspirating means to draw the strands 2a, 2b back in again. Alternatively, it is possible to carry out the above-described procedure by forming a loop with the control rod 3b instead of the control rod 3a and then passing the control rod 3a in a straight condition through the loop formed by the control rod 3b to form the second knot 22.

According to the above-described method, it is possible to easily carry out suturing, ligations and the like in a short time. Furthermore, as the suturing thread is wound automatically, it is possible for one practitioner to perform the procedure using his or her right and left hands to operate, respectively, the knot-forming instruments 1'a, 1'b. Moreover, as opposed to the problems arising from the use of staple-like means, the procedure above involves the use of suturing threads, which makes it possible to carry out safe and reliable suturing, ligation, anastomosis and the like. Also, as it is possible to form two or more knots with a single operation, it becomes possible to increase the strength of the knots formed during such procedures.

Now, by increasing the number of coils in the spiral-shaped loop, it becomes possible to form any number of twist in the knot, which leads to stronger knots. In this regard, by constructing the pulling reel 72 to allow independent rotation of each of the reels 72a, 72b, 72c, 72d, any combination of the wires may be operated, and this makes it possible to select the number of coils that will make up the spiral-shaped loop formed by the bendable portion 32 among one, two or three. With such a construction it is therefore possible to provide a single knot-forming instrument that is capable of forming a variety of knots.

Also, by increasing the number of wires that are manipulated for operating the bendable portion 32, it is possible to add more twists to the second knot formed for securing the first knot.

Next, a description will be given below for a third embodiment of a knot-forming instrument according to the present invention. In this regard reference will be made to FIGS. 19, 20, and 21, which illustrate partial perspective views of the third embodiment of the knot-forming instrument according to the present invention. Now, in the description given below for the third embodiment, the same reference marks and characters that were used for the first embodiment will be used to indicate the same elements or components, and therefore a detailed description of such elements will be omitted.

The knot-forming instrument 8, according to the third embodiment of the present invention, comprises a pair of identical control rods 3a, 3b and control device (not shown in the figures) for remote controlling the control rods 3a, 3b. In this embodiment, the control device comprises handle means 37, winding mechanisms 6, bending motion control mechanisms 7, aspirating means and the like which are provided as paired elements. These elements can be operated independently for the control rods 3a, 3b to carry out bending of the bendable portion 32, aspirating of the strands 2a, 2b, pulling, winding, tensioning, cutting and other such operations.

Provided in the vicinity of the control apparatus is a bundling tube 9 in which base portions of the control rods 3a, 3b are housed so as to allow the control rods 3a, 3b to be movable along the axial direction thereof. Namely, the control rods 3a, 3b are provided in a bundle so as to pass through the inside of the bundling tube 9 which is adapted to be inserted into a body cavity by being passed through a trocar tube. As for the straight portions 31, bendable portions 32, and the wire arrangements and the like of the control rods 3a, 3b of the knot-forming instrument 8, they have the same construction as the corresponding elements of the knot-forming instrument of the first embodiment.

Now, an example of a knot-forming method using the knot-forming instrument 8 of the present invention having the above-described construction will be described with reference to FIGS. 19 to 21. First, a plurality of trocar tubes are inserted through the abdominal wall, which act as communicating tubes for communicating the outside of the body with the inside of the body cavity, and in this arrangement the bundling tube 9 with the control rods 3a, 3b both in a straight condition are inserted as a single tube body 8 through one of the trocar tubes. As seen in the drawings, two threads 2a, 2b are seen in a state after they have passed through body tissue, for example, after they have been used to suture body tissue by a suturing instrument passed through one of the other trocar tubes.

Figure 19:
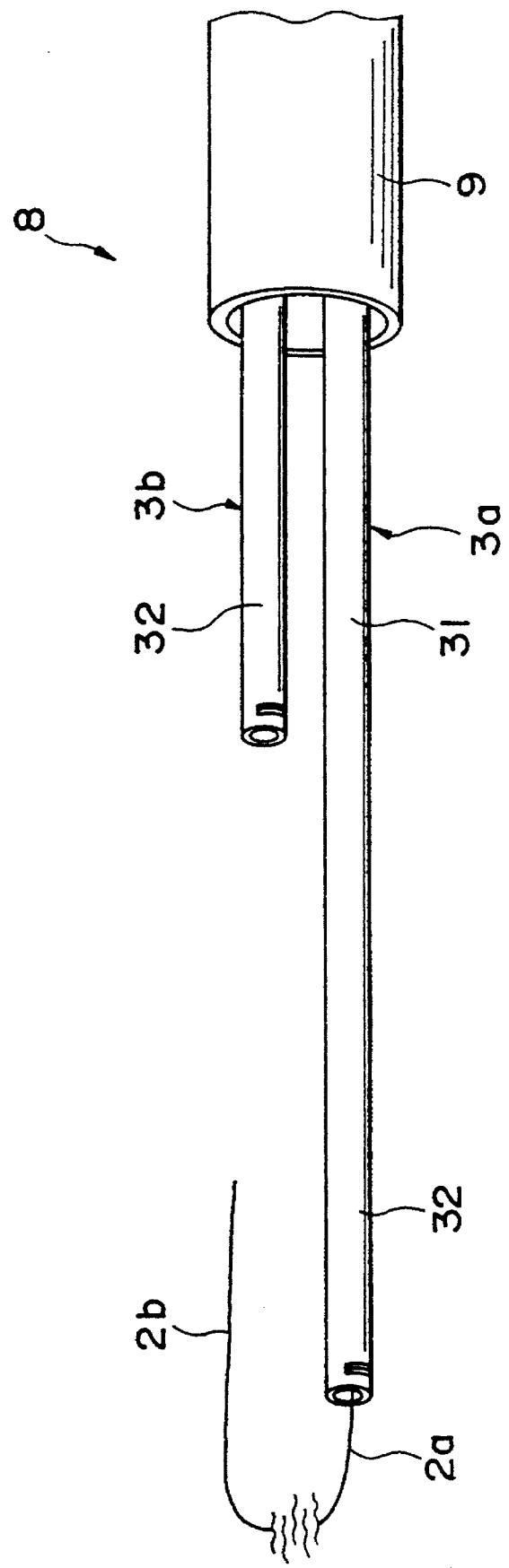
FIG. 19 is a perspective view of a portion of a third embodiment of a knot forming instrument according to the present invention, in which the condition where both the control rods are in the straight condition is shown.

In a manner similar to that described above, the winding mechanism 6 is operated, and as shown in FIG. 19, by activating the aspirating means, a strand 2a of the suturing thread 2 that has been passed through body tissue is sucked inside the tip end of the control rod 3a of the knot-forming instrument 8, and is then securely held and wound by the winding mechanism 6. Then after the strand 2a has been wound, the winding mechanism 6 is locked against further movement.

Figure 20:
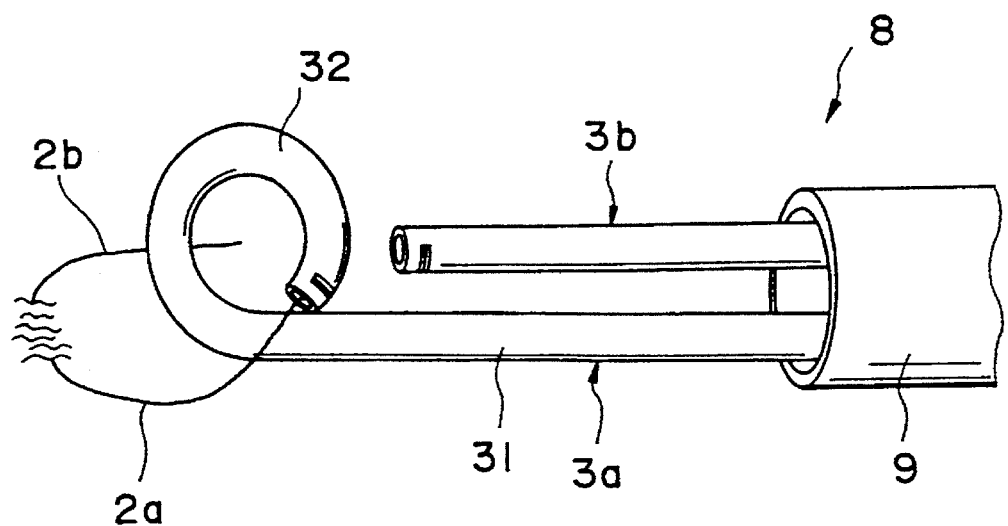
FIG. 20 is a perspective view showing the condition that a knot is being formed by utilizing the third embodiment of the knot forming instrument.

Then, as shown in FIG. 20, by operating the pulling reel, the bendable portion 32 of the control rod 3a is bent to form an α-shaped loop. Next, by operating the winding reel, the thus-formed loop is inclined with respect to the straight portion 31.

Figure 21:
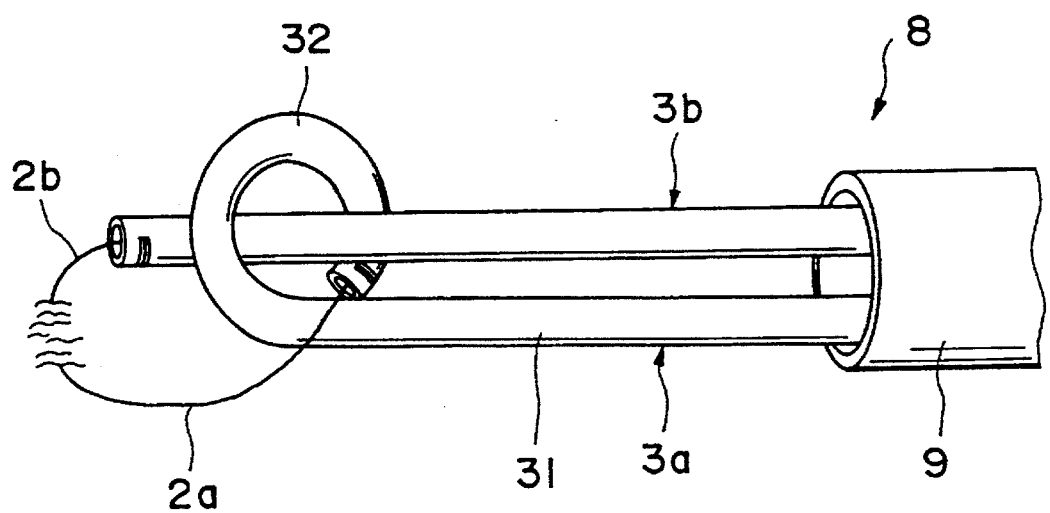
FIG. 21 is a perspective view showing the condition that a knot is being formed by utilizing the third embodiment of the knot forming instrument.

Next, as shown in FIG. 21, while being maintained in a straight condition, the end of the bendable portion 32 of the control rod 3b is passed through the inside of the loop-shaped bendable portion 32. In this state, the aspirating means is employed to suck a strand 2b of the suturing thread 2 into the tip end of the control rod 3b to be held securely by the winding mechanism 6. Then the tip end of the control rod 3b is retracted to a position where the tip end is in out of the loop. After these steps have been completed, first and second knots are formed with the strands 2a, 2b in the same way as described in the example set forth above for the first embodiment of the present invention.

By using the knot-forming instrument 8 described above, the operations of the control rods 3a, 3b are simplified as a result of their being bundled together in a single bundling tube 9. Moreover, this arrangement makes it possible to reduce the number of trocar tubes need to perform a surgical operation, because only one trocar tube is needed for inserting the control rods 3a, 3b into a body cavity, and this reduces the burden on the patient.

In this regard, as modifications of the knot-forming instrument 8 of the third embodiment, it is possible for at least one of the control rods 3a, 3b to be provided with a bendable portion 32 similar to that described for the second embodiment, namely, a bendable portion 32 that can be formed into a spiral loop (coiled state). Further, it is also possible to constitute one of the control rods 3a, 3b so as not to provide with any bendable portion 32, that is to say its tip portion may be constructed so as not to be bendable.

Next, a description will be given below for a fourth embodiment of a knot-forming instrument according to the present invention. In this regard, reference will be made to FIGS. 22 to 29, which illustrate perspective views of a knot-forming process that utilizes the knot-forming instrument according to the fourth embodiment of the present invention. Now, in the description given below for the fourth embodiment, the same reference marks and characters that were used for the first embodiment will be used to indicate the same elements or components, and therefore a detailed description of such elements will be omitted.

The knot-forming instrument 10, according to the fourth embodiment of the present invention, comprises a pair of control rods 3c, 3d, a control device (not shown in the figures) for remote controlling the control rods 3c, 3d and a bundling tube 9 that is the same as that provided for the third embodiment. Inside the bundling tube 9, the base portions of the control rods 3c, 3d are housed so as to allow the control rods 3c, 3d to be movable along the axial direction thereof. Namely, the control rods 3c, 3d are provided in a bundle so as to pass through the inside of the bundling tube 9 which is adapted to be inserted into a body cavity by being passed through a trocar tube.

Figure 22:
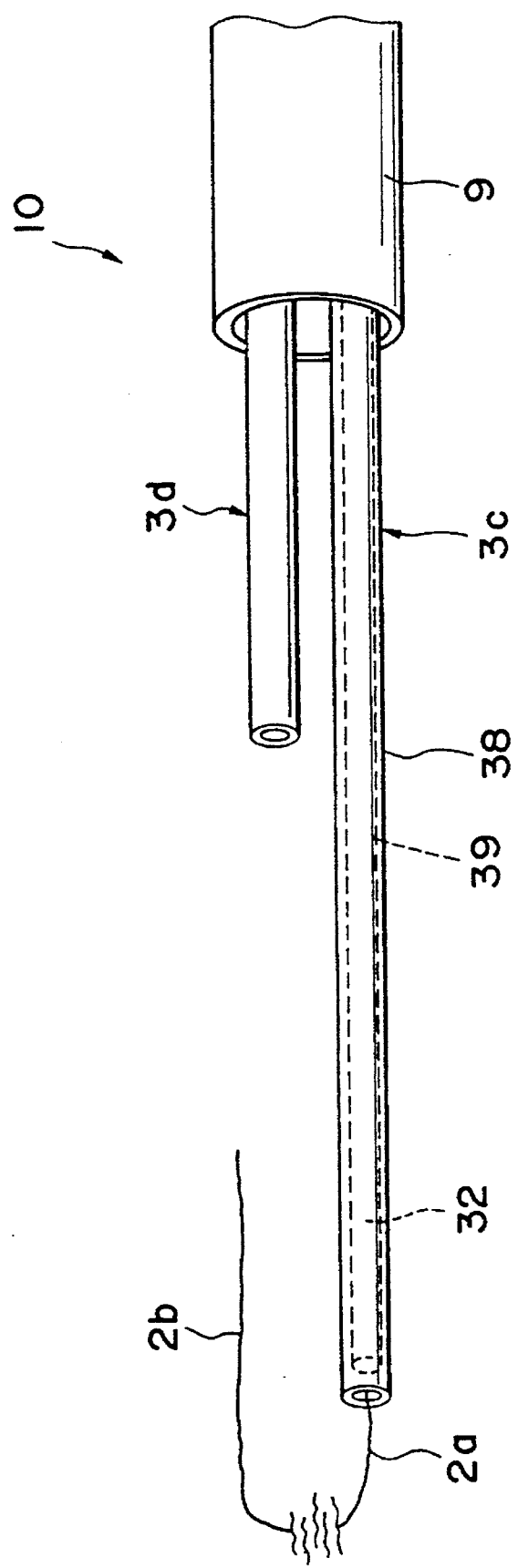
FIG. 22 is a perspective view of a portion of a fourth embodiment of a knot forming instrument according to the present invention, in which the condition where both the control rods are in the straight condition is shown.
Figure 23:
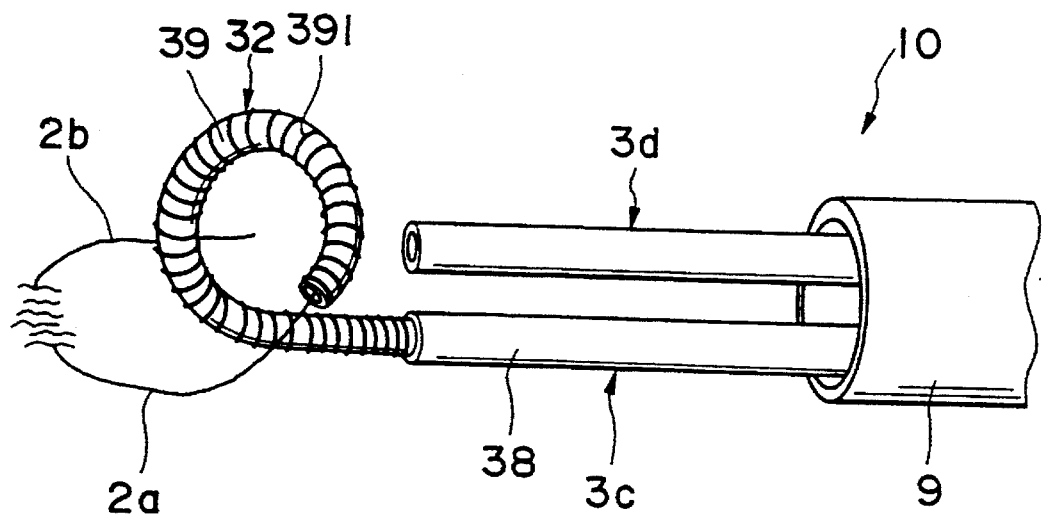
FIG. 23 is a perspective view showing the condition that a first knot is being formed by utilizing the fourth embodiment of the knot forming instrument.
Figure 24:
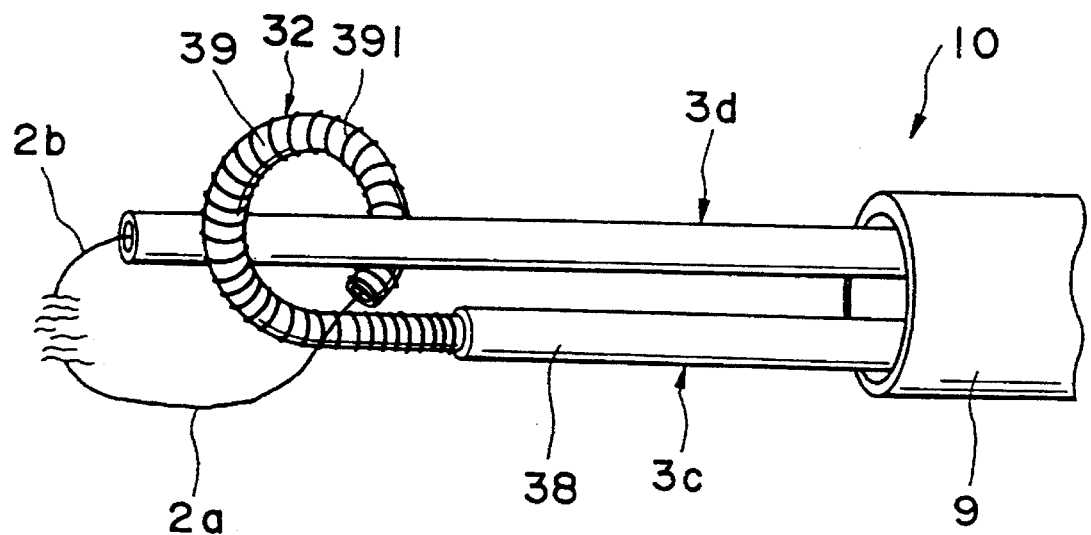
FIG. 24 is a perspective view showing the condition that the first knot is being formed by utilizing the fourth embodiment of the knot forming instrument.

The control rod 3c comprises an outer tube 38 constructed from a rigid material and an inner tube 39 which passes through the inside of the outer tube 38. The inner tube 39 has a flexible tip end portion functioning as a bendable portion 32. Around the flexible end portion of the inner tube 39, a coil 391 for producing a bending condition is wound so that when the end portion of the inner tube 39 is pushed to the outside of the outer tube 38 and no external force is applied there to, as shown in FIGS. 23 and 24, the bendable portion 32 forms a prescribed loop due to the natural elasticity of the coil 391 wound around the end portion of the inner tube 39. Then, as shown in FIG. 22, when the inner tube 39 is moved to bring the end portion thereof into the inside of the outer tube 38, the bendable portion 32 is regulated by the outer tube 39, and restored its straight condition.

As for the material used to construct the coil 391, examples include stainless steel such as SUS316, SUS304, precipitation hardening stainless (PH stainless) or the like, metal alloys having high elasticity such as Ni-Ti alloy or the like, and resinous materials such as polyamide, polyimide, polyethylene, polyarylate resin, polytetrafluoroethylene or the like.

With regards to the control rod 3d, it is constructed as a straight tube body of which tip portion is not bendable.

Provided at the base end of the control rods 3c, 3d is a control device that comprises winding mechanisms 6, aspirating means and the like provided as paired elements that can be operated independently for the control rods 3c, 3d for carrying out axially-directed movement of the control rods 3c, 3d, aspiration of the strands 2a, 2b, pulling, winding, tensioning and other such operations. The control device is also equipped with a bending motion control mechanism for controlling the bending of the bending portion 32. In this embodiment, there is no need for the bendable control mechanism to have the previously described plurality of wires and pulling means comprised of reels 71, 72. Instead, there is provided a mechanism by which the bendable portion 32 of the inner tube 39 is straightened or formed into a loop by moving the inner tube 39 with respect to the axial direction of the outer tube 38 to, respectively, house the bendable portion 32 inside the outer tube 38 or push the bendable portion 32 out of the outer tube 38.

Now, an example of a knot-forming method using the knot-forming instrument 10 of the present invention having the above-described construction will be described with reference to FIGS. 22 to 29. First, a plurality of trocar tubes are inserted through the abdominal wall, and in this arrangement the control rods 3c, 3d are both maintained in a straight condition and they are inserted together with the bundling tube 9 through one of the trocar tubes. In this state, the bendable portion 32 is housed within the outer tube 38 of the control rod 3c. As seen in the drawings, two threads 2a, 2b are shown in a state after they have passed through body tissue, for example, after they have been used to suture body tissue by a suturing instrument passed through one of the other trocar tubes.

In a manner similar to that described above for the example of the third embodiment, by activating the aspirating means, a strand 2a of the suturing thread 2 that has been passed through body tissue is sucked inside the tip end of the control rod 3c of the knot-forming instrument 1a, as shown in FIG. 22, and is then securely held and wound by the winding mechanism 6. Then after the strand 2a has been wound, the winding mechanism 6 is locked against further movement.

Then, as shown in FIG. 23, by retracting the outer tube 38 of the control rod 3c toward its base side such that the bendable portion 32 is protruded from the tip end of the outer tube 38. In this state, the bendable portion 32 bends to form an α-shaped loop.

Next, as shown in FIG. 24, the control rod 3d is passed through the inside of the loop-shaped bendable portion 32. In this state, the aspirating means is employed to suck the strand 2b of the suturing thread 2 into the tip end of the control rod 3d to be held securely by the winding mechanism 6. In this state, the control rod 3c is retracted to a position where the tip end thereof is in out of the loop.

Figure 25:
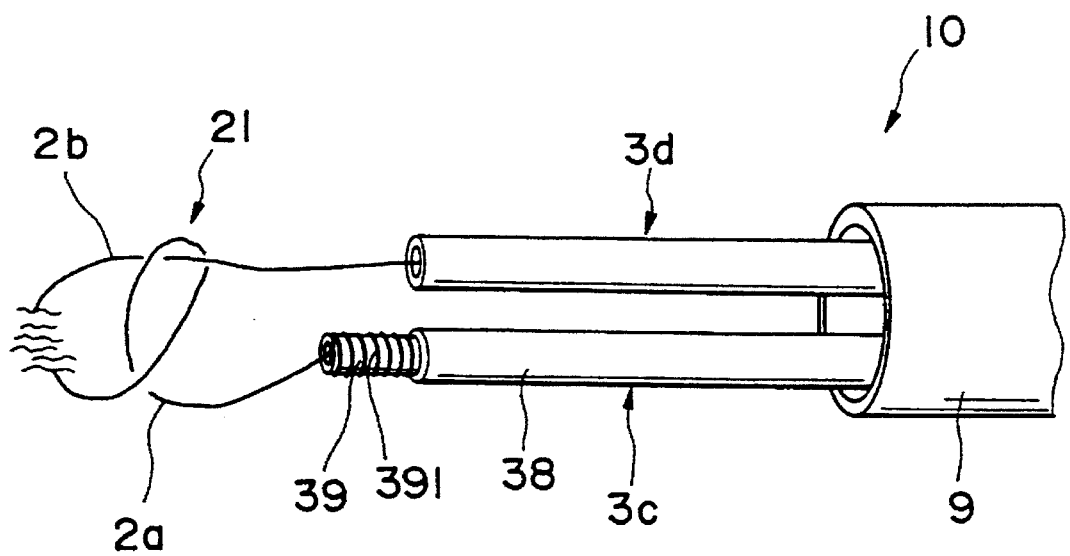
FIG. 25 is a perspective view showing the condition that the first knot is being formed by utilizing the fourth embodiment of the knot forming instrument.

Then, as shown in FIG. 25, the inner tube 39 of the control rod 3c is pulled to bring the bendable portion 32 back inside the outer tube 38, and this results in the strands 2a, 2b being wound around each other to form a first knot 21. Finally, if necessary, in the same manner as the previous embodiments, the winding mechanism 6 is operated to pull the strand 2a which causes the control rods 3c, 3d to move towards the tissue being sutured, and this results in the knot 21 being tightened against the tissue to enable the forming of a secure knot.

Figure 26:
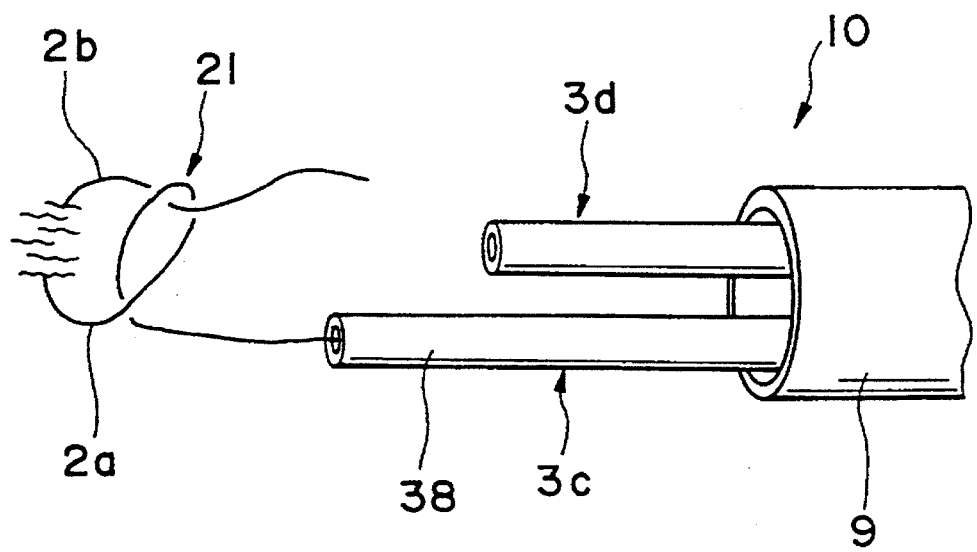
FIG. 26 is a perspective view showing the condition that a second knot is being formed by utilizing the fourth embodiment of the knot forming instrument.
Figure 27:
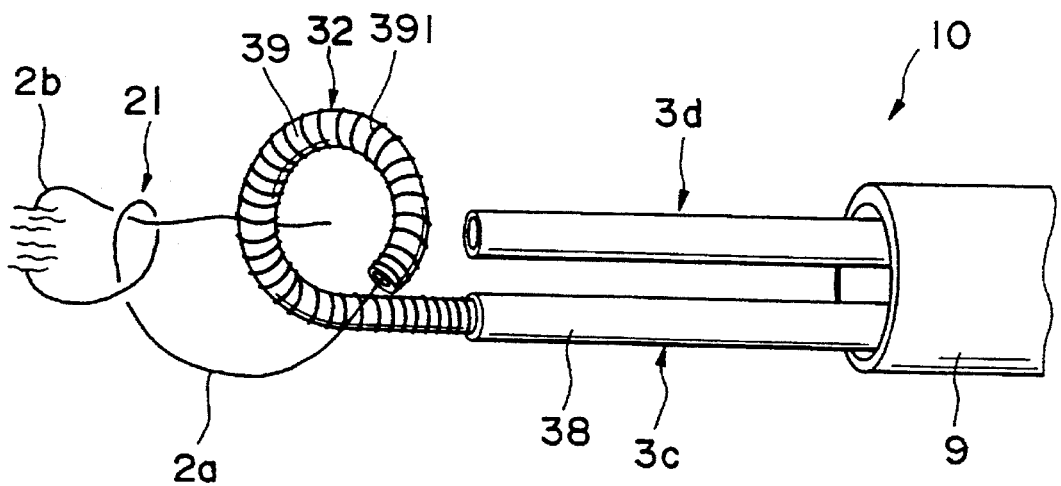
FIG. 27 is a perspective view showing the condition that the second knot is being formed by utilizing the fourth embodiment of the knot forming instrument.

Next, as shown in FIG. 26, after the winding mechanism 6 is unlocked and the strands 2a, 2b are slackened, the strand 2b is blown out of the control rod 3d using the same method as was employed in the previous embodiments. Then, as shown in FIG. 27, the inner tube 39 of the control rod 3c is moved once more to cause the bendable portion 32 thereof to be pushed out of the outer tube 38, which results in the bendable portion 32 forming a loop.

Figure 28:
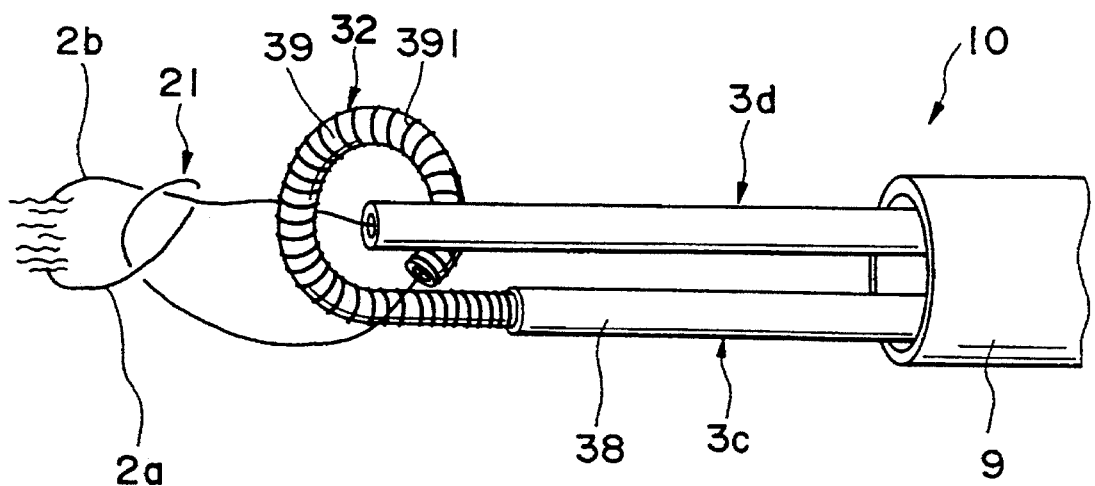
FIG. 28 is a perspective view showing the condition that the second knot is being formed by utilizing the fourth embodiment of the knot forming instrument.

Then, as shown in FIG. 28, the control rod 3d is forwarded so as to pass through the inside of the loop-shaped bendable portion 32. In this state, the aspirating means is employed to suck the strand 2b into the tip end of the control rod 3d to be held securely by the winding mechanism 6.

Figure 29:
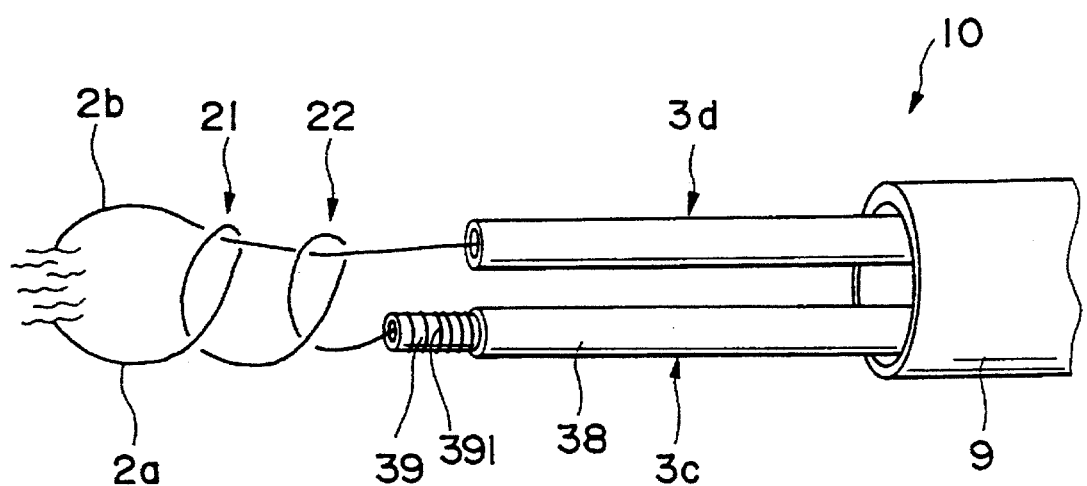
FIG. 29 is a perspective view showing the condition that the second knot is being formed by utilizing the fourth embodiment of the knot forming instrument.
Figure 30:
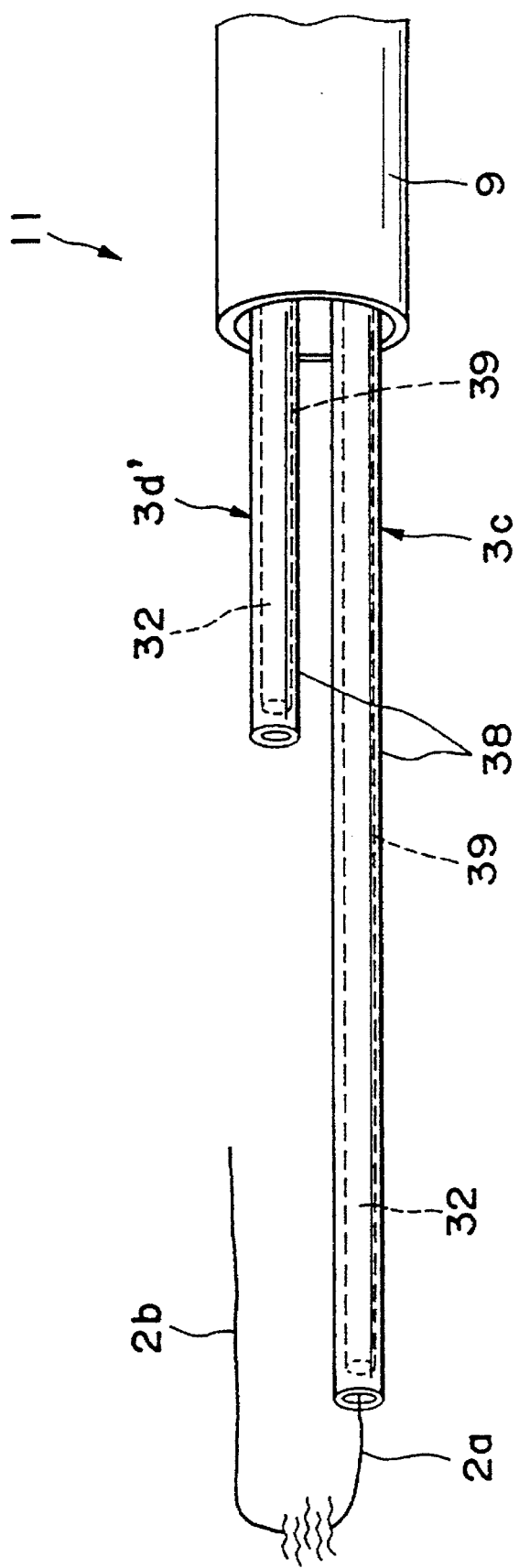
FIG. 30 is a perspective view of a portion of a fifth embodiment of a knot forming instrument according to the present invention.

Next, as shown in FIG. 29, the inner tube 39 of the control rod 3c is pulled to bring the bendable portion 32 back inside the outer tube 38, and this results in the strands 2a, 2b being wound around each other to form a second knot 22. Finally, in the same manner as the previous embodiments, the winding mechanism 6 is operated to pull the strands 2a, 2b, which causes the control rods 3c, 3d to move towards the tissue being sutured, and this results in the second knot 22 being tightened against the tissue to enable to form a secure knot.

By using the knot-forming instrument 10 described above, in addition to obtaining the same advantages that are obtained with the knot-forming instrument 8, there is the advantage that in order to bend the bendable portion 32 into a loop, there is no need for wires and their corresponding pulling reels and the like. Also, the control rod 3d does not need to be provided with a bendable portion. Therefore, this arrangement makes it possible to reduce the diameters of the control rods 3c, 3d. Further, the operation required for bending the bendable portion is quite easy. Moreover, as the normal condition of the bendable portion 32 is that of a prescribed loop, there is the advantage that the loop can be easily formed so as to have a consistent shape.

Now, with regards to modifications of the knot-forming instrument 10 of the fourth embodiment, it is possible for the control rods 3c to be provided with a bendable portion 32 similar to that described for the second embodiment, namely, a bendable portion 32 that can be formed into a spiral loop (coiled state).

Next, a description will be given below for a fifth embodiment of a knot-forming instrument according to the present invention. In this regard, reference will be made to FIGS. 30 to 33, which illustrate partial perspective views of the knot-forming instrument according to the fifth embodiment of the present invention. Now, in the description given below for the fourth embodiment, the same reference marks and characters that were used for the fourth embodiment will be used to indicate the same elements or components, and therefore a detailed description of such elements will be omitted.

The knot-forming instrument 11, according to the fifth embodiment of the present invention, comprises a pair control rods 3c, 3d', a control device (not shown in the figures) for remote controlling the control rods 3c, 3d' and a bundling tube 9 that is the same as that provided for the fourth embodiment.

As for the control rod 3d', it has the same construction as the control rod 3c. However, in this embodiment the bendable portion 32 of the control rod 3c and the bendable portion 32 of the control rod 3d' form loops that curve in opposite directions with respect to each other.

Provided at the base end of the control rods 3c, 3d' is the control device that comprises winding mechanisms 6, aspirating means, bending control mechanisms and the like provided as paired elements that can be operated independently for the control rods 3c, 3d' for carrying out axially-directed movement of the control rods 3c, 3d', bending of the bendable portions 32, aspiration of the strands 2a, 2b, pulling, winding, tensioning and other such operations. The control device is also equipped with a bending motion control mechanism for controlling the bending of the bending portion 32.

Now, an example of a knot-forming method using a knot-forming instrument 11 of the present embodiment having the above-described construction will be described with reference to FIGS. 30 to 33. First, a plurality of trocar tubes are inserted through the abdominal wall. In this arrangement the control rods 3c, 3d' are inserted into one of trocar tubes together with the bundling tube 9. In this state, the bendable portions 32 are housed within their respective outer tubes 38 to maintain its straight condition, respectively. As seen in the drawings, two threads 2a, 2b are shown in a state after they have passed through body tissue, for example, after they have been used to suture body tissue by a suturing instrument passed through one of the other trocar tubes. These strands 2a, 2b are then used to form a first knot 21 in the same way as was described above for the example of the fourth embodiment.

Figure 31:
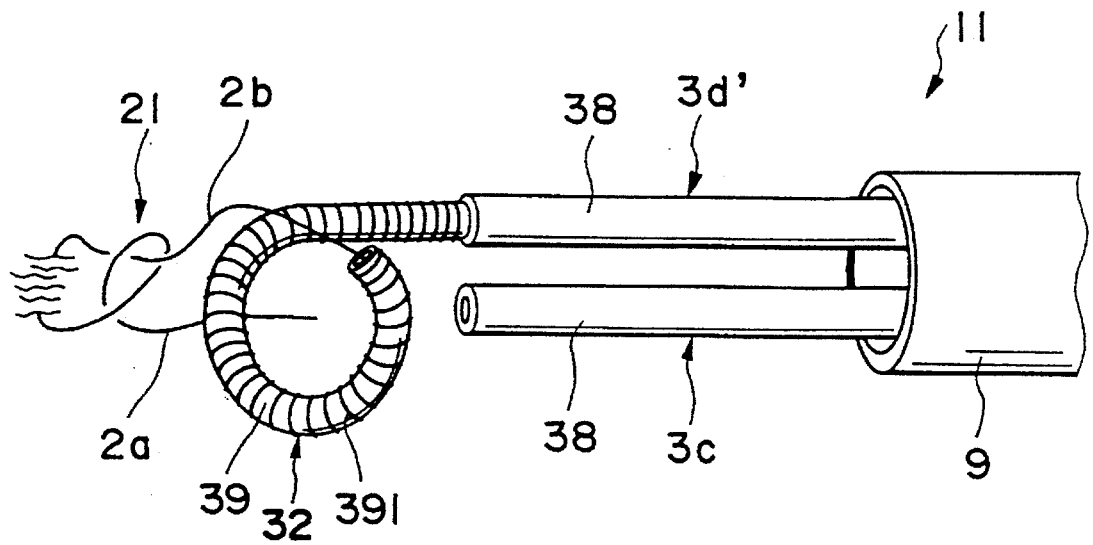
FIG. 31 is a perspective view showing the condition that a second knot is being formed by utilizing the fifth embodiment of the knot forming instrument.

Next, as shown in FIG. 31, after the winding mechanism 6 is unlocked and the strands 2a, 2b are slackened, the strand 2a is blown out of the control rod 3d' using the same method as was employed in the previous embodiments. Then, while the bendable portion 32 of the control rod 3c is housed inside the outer tube 38, the inner tube 39 of the control rod 3d' is moved to cause the bendable portion 32 thereof to be pushed out of the outer tube 38, which results in the bendable portion 32 of the control rod 3d' forming an α-shaped loop that twists in the opposite direction to the loop formed from the bendable portion 32 of the control rod 3c.

Figure 32:
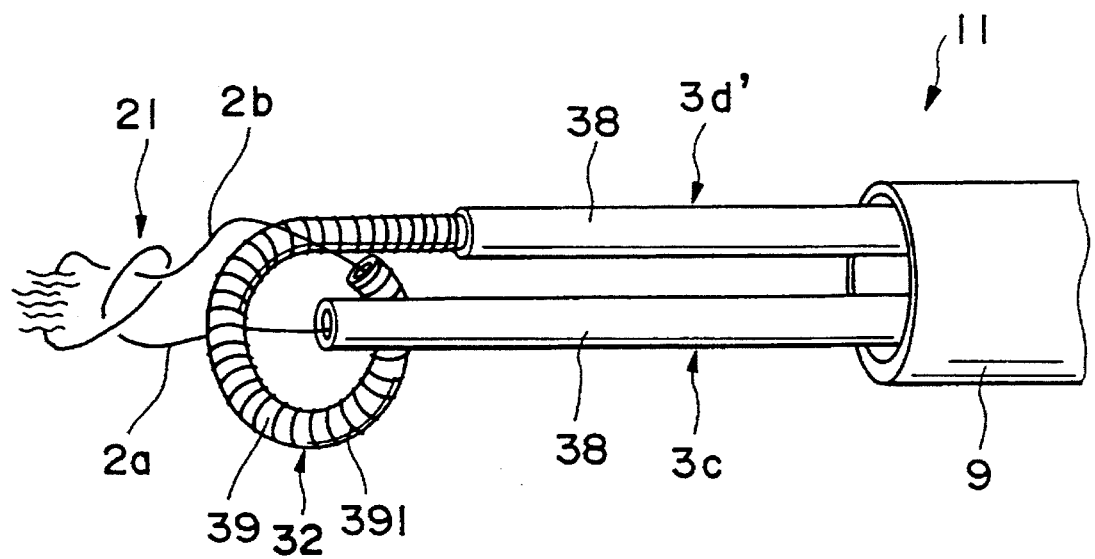
FIG. 32 is a perspective view showing the condition that the second knot is being formed by utilizing the fifth embodiment of the knot forming instrument.

Then, as shown in FIG. 32, the control rod 3c is forwarded so as to pass through the inside of the loop-shaped bendable portion 32 of the control rod 3d'. In this state, the aspirating means is employed to suck the strand 2a into the end of the control rod 3c to be held securely by the winding mechanism 6.

Figure 33:
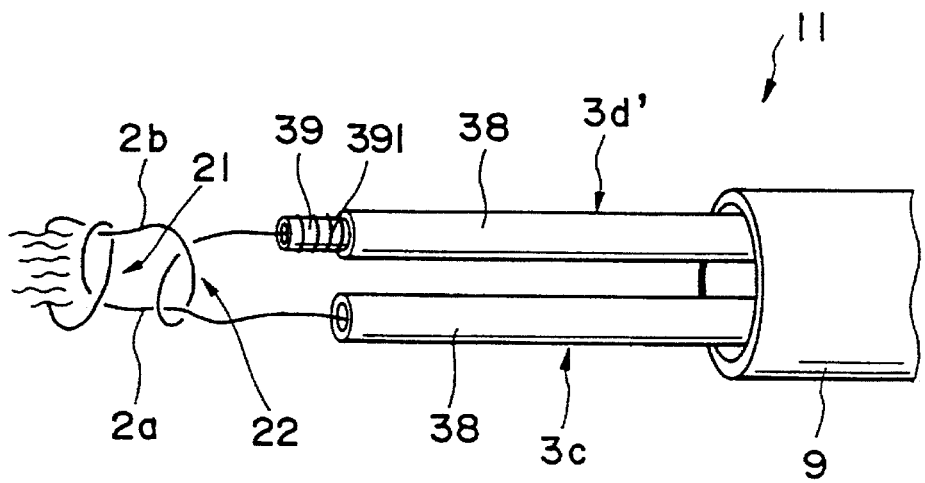
FIG. 33 is a perspective view showing the condition that the second knot is being formed by utilizing the fifth embodiment of the knot forming instrument.

Next, as shown in FIG. 33, the inner tube 39 of the control rod 3d' is pulled to bring the bendable portion 32 thereto back inside the outer tube 38, and this results in the strands 2a, 2b being wound around each other to form a second knot 22. Finally, in the same manner as the previous embodiments, the winding mechanism 6 is operated to pull the strands 2a, 2b to apply tension thereto, which causes the control rods 3c, 3d' to move towards the tissue being sutured, and this results in the second knot 22 being tightened against the tissue to enable the forming of a secure knot.

Now, another example of a knot-forming method using the knot-forming instrument 11 of the present embodiment having the above-described construction will be described with reference to FIGS. 32 to 35. First, a plurality of trocar tubes are inserted through the abdominal wall. In this arrangement, the control rods 3c, 3d' are inserted into one of the trocar tubes. In this state, the bendable portions 32 are housed within their respective outer tubes 38 to maintain its straight condition, respectively. As seen in the drawings, two threads 2a, 2b are shown in a state after they have passed through body tissue, for example, after they have been used to suture body tissue by a suturing instrument passed through one of the other trocar tubes. These strands 2a, 2b are then used to form a first knot 21 in the manner described below.

First, by activating the aspirating means, a strand 2b of the suturing thread 2 that has been passed through body tissue is sucked inside the end of the control rod 3d' of the knot-forming instrument 11, and is then securely held and wound by the winding mechanism 6.

Figure 34:
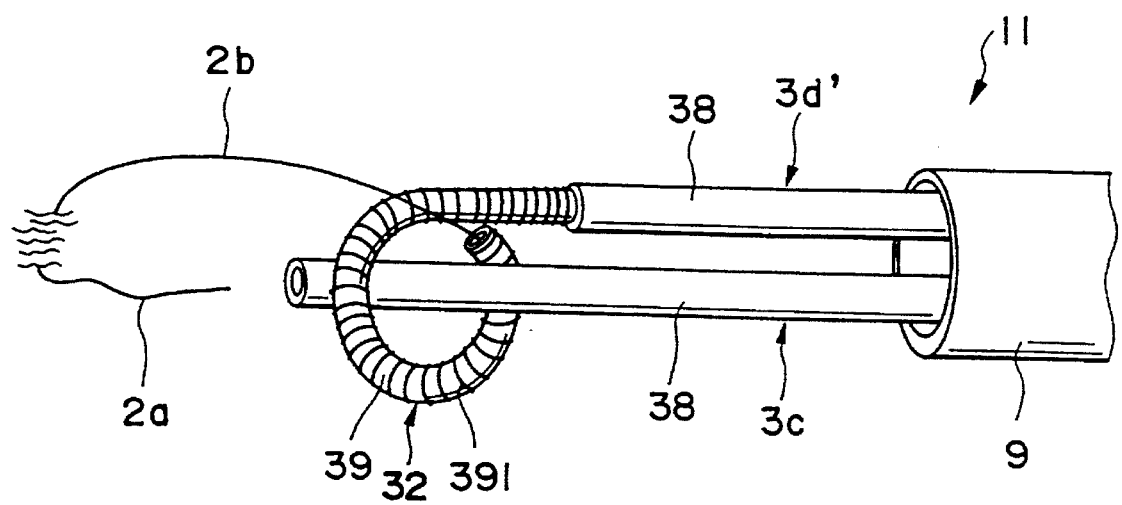
FIGS. 34–35 are perspective views showing different methods for forming a knot utilizing the fifth embodiment of the knot forming instrument.

Next, by pushing the inner tube 39 of the control rod 3d' out of the outer tube 38, the bendable portion 32 of the control rod 3d' bends to form an α-shaped loop. Then, as shown in FIG. 34, the control rod 3c is forwarded so as to pass through the inside of the loop-shaped bendable portion 32 of the control rod 3d'.

Figure 35:
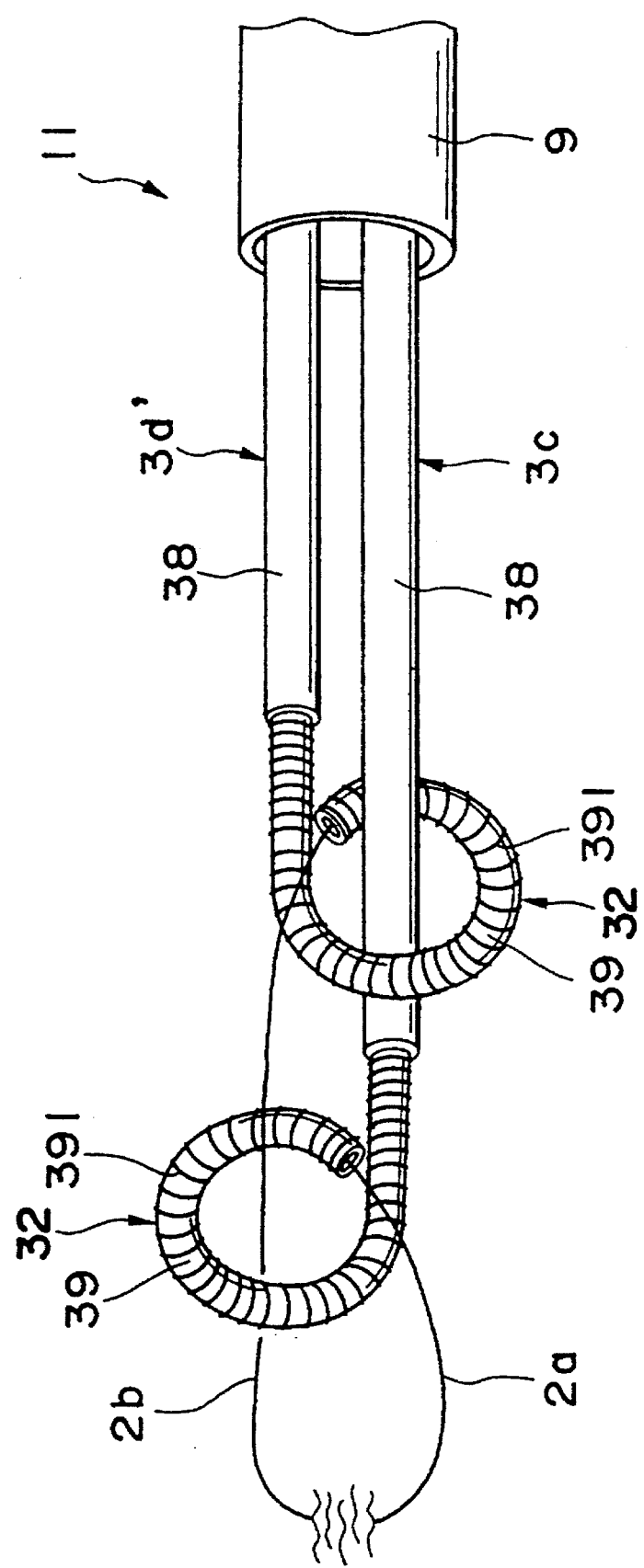

Then, as shown in FIG. 35, the inner tube 39 of the control rod 3c is pushed out of the outer tube 38, which causes the bendable portion 32 of the control rod 3c to form an α-shaped loop that surrounds the strand 2b. After this step has been carried out, the aspirating means is employed to suck the strand 2a of the suturing thread 2 into the tip end of the control rod 3c to be held securely by the winding mechanism 6.

Next, the inner tube 39 of the control rod 3c is moved so as to house the bendable portion 32 back inside the outer tube 38, and, at the same time, the control rod 3c is slightly retracted in the direction towards its base end. In this way, as shown in FIG. 32, the strands 2a, 2b are made to cross each other to form the first knot 21.

Now, from the state shown in FIG. 32, as the control rod 3c is further moved toward its base end, the tip end thereof is pulled through the loop-shaped bendable portion 32 of the control rod 3d'. At the same time, the inner tube 39 of the control rod 3d' is moved so as to house the bendable portion 32 thereof back inside its outer tube 38. In this way, the strands 2a, 2b are made to cross each other to form the second knot 22. Then as was done before, the second knot 22 is tightened against the tissue to enable the forming of a secure knot.

By using the above method, it is possible to form first and second knots 21, 22 without having to discharge the introduced strands 2a, 2b from the insertion paths of the control rods 3c, 3d'. This makes it possible to carry out the knot-forming process with ease at a reduced procedure time.

As the modification of a knot-forming instrument 11, it is possible to provide at least one of the control rods 3c, 3d' with a bendable portion that can form a spiral-shaped loop (coiled shape) in the same manner as the second embodiment.

In these preferred embodiments, before forming a knot by the knot forming instruments, it is possible to bring first and second threads into a body cavity by the instruments, and then to form a knot in the same manner as these embodiments after suturing or ligation is carried out to a body tissue with the threads by utilizing forceps, suturing instruments or ligating instruments.

Further, in these preferred embodiments described above, the suture thread introducing means is not limited to the aspirating means. Instead, it is also possible to employ a plurality of paired pulling rollers provided in series inside the control rods to introduce the thread by driving these roller sequentially.

Moreover, it is possible to employ a guide wire that can be inserted into the insertion path 30 from the side of control device 4. In this case, the guide wire would be provided with a hook or other type of grasping means that can be used to catch the suturing thread. According to this modification, after the wire is caught by the hook, the guide wire can be pulled into the control rod 3 together with the thread, to take up the thread.

As for the bent shape of the bending portion 32, it does not need to form a complete loop as in the case of the α-shaped loop described above. Instead, any shape that allows another control rod 3 to be inserted therethrough will do. For example, it is possible to carry out the above-described knot-forming methods with the bendable portion 32 formed into a half circle.

Furthermore, the bendable portion 32 may be formed from a plurality of tube bodies 33 each having a different length. In this connection, there is a tendency that a curvature of a base side of the loop-shaped bendable portion becomes greater than that of a tip side thereof when the bendable portion is composed of tube bodies of the same size and thus formed bendable portion is bent into a loop-shape by pulling predetermined wires. However, if the length of each of the tube bodies 33 is appropriately varied, it is possible to make the tip side of the bendable portion easier to be bent. As a result, it becomes possible to form a spairally-shaped loop having a constant curvature by pulling the wires.

As other alternative structure of the bendable portion 32, it is possible to employ a plurality of annular rings as the unit members which construct the bendable portion. These annular rings are coupled with each other by means of coupling axes which are connected to each ring at the opposite diametrical portions thereof, respectively. In this alternative, the bendable portion is constructed from these annular rings and the coupling axes.

Further, the bendable portion may be constructed so as to be bent into one direction selected from upward, downward, rightward and leftward directions. Further, it is also possible to construct the bendable portion so as to be bent into two directions such as upward and downward directions, leftward and rightward directions, upward and rightward directions, upward and leftward directions, downward and rightward directions, or downward and leftward directions or the like. Furthermore, it is also possible to construct the bendable portion 32 so as to be able to be bent into three directions in the same manner as the embodiments described above, or four directions including upward, downward, leftward and rightward directions.

In particular, in these embodiments described above, the tube bodies are coupled with each other through spherically-shaped coupling joints, the directions to which the bendable portion can be bent are no limited to the specific directions mentioned above. Specifically, the bendable portion according to these embodiments can be bent into any arbitrary directions besides the four directions mentioned above. Further, in the bendable portion, since each tube body is constructed so as to be rotatable by itself with respect to the axis, this structure is suitable to form a spirally formed loop.

Furthermore, it is also possible to construct the bendable portion 32 such that the bendable portion which has been bent into a desired shape by the operation of the wires can be restored into its original straight condition automatically. In more detail, the bendable portion 32 can be constructed such that under the original condition it can maintain its original posture (straight condition) as shown in FIGS. 3, 14 and 19 by the biasing force of the biasing members axially disposed, under the condition that the wires are being pulling the bendable portion 32 is bent into the loop shape, and when the wires are released the bendable portion is restored its original posture by means of the function of the biasing members.

Finally, although the invention has been described by exemplifying preferred embodiments, it is no limited to the embodiments, and various changes and modifications within the principle and the scope of the invention will be apparent for those skilled in the art.

What is claimed is:

1. A knot forming instrument which forms a knot of a thread, comprising:

a control rod insertable into a communicating tube which communicates an abdominal cavity with the outside of a body of a patient, said control rod having a base portion and a bendable tip portion;

an insertion path formed inside said control rod and having an opening formed at the bendable tip portion of said control rod;

thread introducing means for introducing thread into the insertion path by sucking one end of the thread through said opening; and a control device provided on said base portion for operating said control rod from outside the body to change said bendable tip portion of said control rod between a substantially straight condition and a bent condition in which the tip portion is bent in at least one direction.

2. The knot forming instrument as claimed in claim 1, wherein said bendable tip portion is bendable to form at least one loop through operation of the control device.

3. The knot forming instrument as claimed in claim 2, wherein said bendable tip portion is bendable to form at least two loops through operation of the control device.

4. The knot forming instrument as claimed in claim 2, wherein said control device includes at least one wire having a tip end that is fixed at a position which is eccentric to an axis of said bendable tip portion, and a bending motion control mechanism for operating said bendable tip portion by pulling said at least one wire toward a base end of the at least one wire, said at least one wire being helically wound with respect to said bendable tip portion from the position at which said tip end of said at least one wire is fixed toward said bending motion control mechanism.

5. The knot forming instrument as claimed in claim 3, wherein said control device includes a plurality of wires each having a tip end fixed at a position which is eccentric to an axis of the bendable tip portion, and a bending motion control mechanism for operating said bendable tip portion by pulling each wire towards a base end of the respective wire, the tip ends of said wires being fixed at positions which are spaced from each other for a predetermined distance along the axial direction of said bendable tip portion, and each wire being helically wound with respect to the bendable tip portion from the position at which the tip end is fixed towards said bending motion control mechanism.

6. The knot forming instrument as claimed in claim 2, wherein the control device includes:

first and second wires each having a tip end, the tip ends of the first and second wires being fixed at positions which are opposed to each other with respect to the axis of said bendable tip portion; and a bending motion control mechanism for bending said bendable tip portion toward a desired direction by pulling said first and second wires towards respective base ends of the first and second wires; said first and second wires being helically wound with respect to said bendable tip portion in opposite directions from the positions where the tip ends of said respective wires are fixed towards the bending motion control mechanism.

7. The knot forming instrument as claimed in claim 6, including a third wire having a tip end that is fixed with respect to said bendable tip portion, and a posture changing mechanism operatively associated with said third wire for changing a posture of a loop formed by the bendable tip portion by pulling said third wire toward a base end of the third wire.

8. The knot forming instrument as claimed in claim 2, wherein said control device includes a wire extending within the control rod and a bending motion control mechanism, said wire having an end connected to the bending motion control mechanism and an opposite end fixed in place at a position along the bendable tip portion.

9. The knot forming instrument as claimed in claim 2, wherein the bendable tip portion includes a plurality of unit members and coupling members for connecting adjacent unit members in a freely pivotable manner, each of said unit members having a thread insertion passage, the entirety of said bendable tip portion being bendable.

10. The knot forming instrument as claimed in claim 2, wherein the thread introducing means includes an aspiration means connected to a base end portion of said insertion path so as to communicate with said insertion path.

11. The knot forming instrument as claimed in claim 2, including tension means disposed between the thread insertion path and the thread introducing means for holding thread introduced into said insertion path and maintaining a tensile force on the thread.

12. The knot forming instrument as claimed in claim 11, wherein said tension means includes a winding axis for winding up thread, a rotatable knob for operatively rotating said winding axis, a biasing member for biasing said winding axis toward a predetermined rotating direction, and a locking member for preventing the winding axis from being rotated against the biasing force of said biasing member.

13. The knot forming instrument as claimed in claim 12, including rotation regulating means operatively associated with said winding axis for regulating the rotation of said winding axis caused by the biasing force of said biasing member.

14. The knot forming instrument as claimed in claim 2, further comprising cutting means provided inside said insertion path for cutting thread extending through said insertion path.

15. The knot forming instrument as claimed in claim 14, wherein the cutting means includes scissors having a pair of blades and arranged at the tip portion of said control rod, a scissors operating wire having bifurcated ends which are secured to end portions opposite to said blades, respectively, and a handle for operatively pulling said scissors operating wire.

16. A knot forming method for forming a knot with first and second threads within an abdominal cavity, comprising the steps of:

inserting first and second control rods into an abdominal cavity through communicating tubes which communicate the abdominal cavity to the outside of a body, each control rod being formed with an insertion path which extends through the control rod, the insertion path having an opening;

introducing a first thread into said insertion path of said first control rod from said opening of said first control rod and holding the first thread;

bending a tip portion of the first control rod by remote control from the outside of the body to form at least one loop;

inserting a tip portion of said second control rod into said loop;

introducing a second thread into said insertion path of said second control rod from the opening of said second control rod and holding the second thread;

inserting the second thread into said loop by pulling out the tip portion of said second control rod from the loop through retraction of said second control rod;

crossing the first thread and the second thread to twist them with each other; and tensioning at least one of the first and second threads to form a first knot.

17. The knot forming method as claimed in claim 16, further comprising the steps of:

releasing said tensioning;

discharging one of the first and second threads outside said insertion path from said opening of the respective control rod;

bending the tip portion of either of said first and second control rods by remote control from the outside of the body to form at least one other loop;

inserting the tip portion of the other control rod into the other loop;

reintroducing the discharged thread into said insertion path of the respective control rod again and holding the thread;

pulling out the tip portion of said other control rod from said other loop by retracting said other control rod and inserting the thread held by said other control rod into said other loop; and crossing the first thread and the second thread to twist them with each other to form a second knot after the first knot has been formed.

18. The knot forming method as claimed in claim 17, further comprising the steps of:

tensioning at least one of the first and second threads after the second knot is formed;

cutting the first and second thread at the tip portions of said first and second control rods, respectively.

19. A knot forming instrument for forming a knot in a thread, comprising:

a control rod positionable in a communicating tube which communicates a body cavity with the outside of the body of a patient, said control rod having a base portion and a bendable tip portion;

an insertion path extending within the control rod and having an opening formed at an end of the bendable tip portion of the control rod;

thread introducing means for introducing a thread into the insertion path from said opening;

at least one wire having one end fixed in place at a position along the bendable tip portion of the control rod and an opposite end; and a bending motion control device to which the opposite end of the at least one wire is connected for imparting a pulling force to the at least one wire to bend the bendable tip portion into a bent condition.

20. The knot forming instrument as claimed in claim 19, wherein said at least one wire extends within said control rod.

21. The knot forming instrument as claimed in claim 19, including a plurality of adjacently positioned tube bodies disposed within the control rod and coupling members interconnecting adjacent tube bodies to permit the tube bodies to freely pivot relative to the coupling members.

22. The knot forming instrument as claimed in claim 19, wherein said at least one wire is fixed to one of said coupling members.

23. The knot forming instrument as claimed in claim 19, wherein said thread introducing means is an aspiration device which communicates with said insertion path for sucking a thread through the opening and into the insertion path.

* * * * *

UNITED STATES PATENT AND TRADEMARK OFFICE
CERTIFICATE OF CORRECTION

PATENT NO. : 5,496,331
DATED : March 5, 1996
INVENTOR(S) : Zhongren XU et al

It is certified that error appears in the above-indentified patent and that said Letters Patent is hereby corrected as shown below:

In Column 6, line 49, delete "both".

In Column 10, line 32, delete "In" and insert -- in --.

In Column 12, line 18, delete "g-shaped" and insert -- $\alpha$-shaped --.

In Column 18, line 30, delete "1$b$" and insert -- 1'$b$ --.

Signed and Sealed this

Second Day of July, 1996

Attest:

BRUCE LEHMAN

Attesting Officer

Commissioner of Patents and Trademarks